(12) United States Patent
Graham et al.

(10) Patent No.: US 9,414,873 B2
(45) Date of Patent: Aug. 16, 2016

(54) MODULAR BONE FIXATION SYSTEM

(75) Inventors: Thomas J. Graham, Novelty, OH (US); Shawn D. Roman, Oviedo, FL (US); William F. Warrender, Collegeville, PA (US); Lance N. Terrill, Oviedo, FL (US); Dinesh Koka, Orlando, FL (US); Matthew D. Schultz, Orlando, FL (US)

(73) Assignee: The Cleveland Clinic Foundation, Cleveland, OH (US)

( * ) Notice: Subject to any disclaimer, the term of this patent is extended or adjusted under 35 U.S.C. 154(b) by 167 days.

(21) Appl. No.: 13/367,328

(22) Filed: Feb. 6, 2012

(65) Prior Publication Data

US 2013/0178905 A1 Jul. 11, 2013

Related U.S. Application Data

(60) Provisional application No. 61/583,527, filed on Jan. 5, 2012.

(51) Int. Cl.
*A61B 17/80* (2006.01)

(52) U.S. Cl.
CPC ........... *A61B 17/808* (2013.01); *A61B 17/8085* (2013.01)

(58) Field of Classification Search
CPC .......................... A61B 17/8085; A61B 17/808
USPC .................................................. 606/282–285
See application file for complete search history.

(56) References Cited

U.S. PATENT DOCUMENTS

| | | |
|---|---|---|
| 1,105,105 A | 7/1914 | Sherman |
| 2,580,821 A | 1/1952 | Nicola |
| 2,780,223 A | 2/1957 | Haggland |
| 3,593,709 A | 7/1971 | Halloran |
| 4,364,382 A | 12/1982 | Mennen |
| 4,429,690 A | 2/1984 | Angelino-Pievani |
| 5,487,741 A | 1/1996 | Maruyama |
| 6,093,188 A | 7/2000 | Murray |
| 6,200,321 B1 | 3/2001 | Orbay |
| 6,273,892 B1 | 8/2001 | Orbay |
| 6,364,881 B1 | 4/2002 | Apgar |
| 7,896,886 B2 | 3/2011 | Orbay |
| 2002/0128654 A1* | 9/2002 | Steger et al. .................... 606/69 |
| 2005/0192578 A1 | 9/2005 | Horst |

(Continued)

FOREIGN PATENT DOCUMENTS

| | | |
|---|---|---|
| WO | WO2009092830 | 7/2009 |
| WO | WO2009100310 | 8/2009 |

OTHER PUBLICATIONS

Acumed Surgical Technique Brochure MHS00_01_A_11_2008.

(Continued)

*Primary Examiner* — David Bates
*Assistant Examiner* — Olivia C Chang
(74) *Attorney, Agent, or Firm* — Tarolli, Sundheim, Covell & Tummino LLP

(57) ABSTRACT

Systems for modular bone fixation may include first, second, and at least one third portion to aid in fracture reduction, simplify the surgical procedure, increase fracture fixation strength, and reduce irritation to the patient caused by the implant. In some examples, the at least one third portion may be separable from the first and second portions to further simplify the surgical procedure and reduce irritation to the patient.

27 Claims, 24 Drawing Sheets

(56) References Cited

U.S. PATENT DOCUMENTS

| | | |
|---|---|---|
| 2005/0288790 A1 | 12/2005 | Swords |
| 2006/0235407 A1* | 10/2006 | Wang et al. .................. 606/69 |
| 2007/0270885 A1 | 11/2007 | Weinert |
| 2008/0015589 A1 | 1/2008 | Hack |
| 2008/0243191 A1 | 10/2008 | Tipirneni |
| 2010/0069966 A1 | 3/2010 | Castaneda |
| 2010/0217328 A1 | 8/2010 | Terrill |
| 2011/0060372 A1 | 3/2011 | Allison |
| 2011/0152946 A1 | 6/2011 | Frigg |
| 2012/0226320 A1* | 9/2012 | Kang et al. .................. 606/283 |
| 2013/0090695 A1* | 4/2013 | Bernstein et al. ............ 606/281 |

OTHER PUBLICATIONS

Medartis Hand Webpage Oct. 6, 2011.
Medartis Hand 1.2/1.5 Product Page (Webpage) Oct. 7, 2011.
Osteomed M3-X Extremity Fixation System Webpage Oct. 7, 2011.
SBI Product Brochure Universal hand System MKT 30320 Rev. A Feb. 2006.
Stryker Product Brochure Stryker hand Plating System May 2011.
Synthes Product Brochure Modular Mini Fragment LCP System. J7545-E (2007).

\* cited by examiner

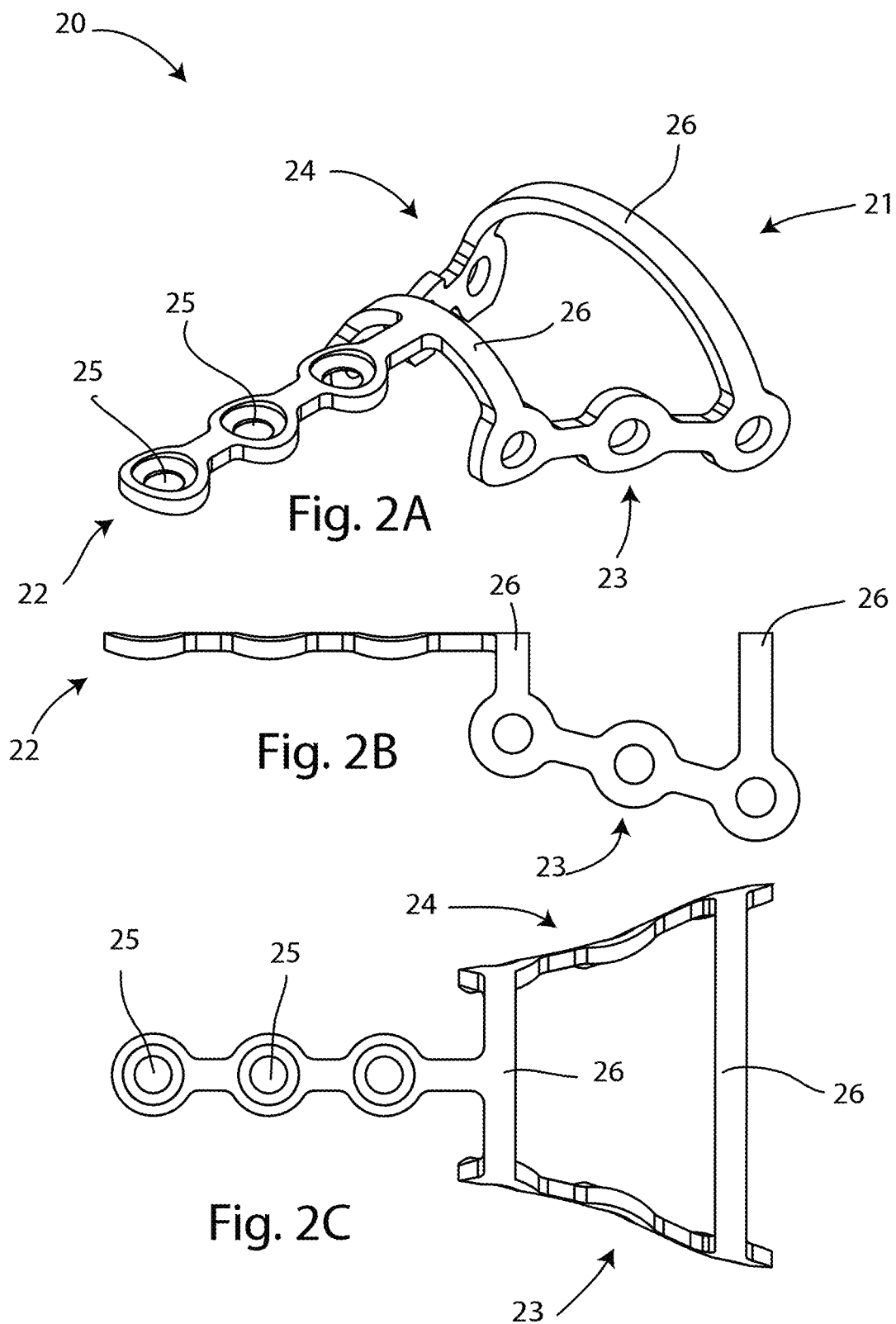

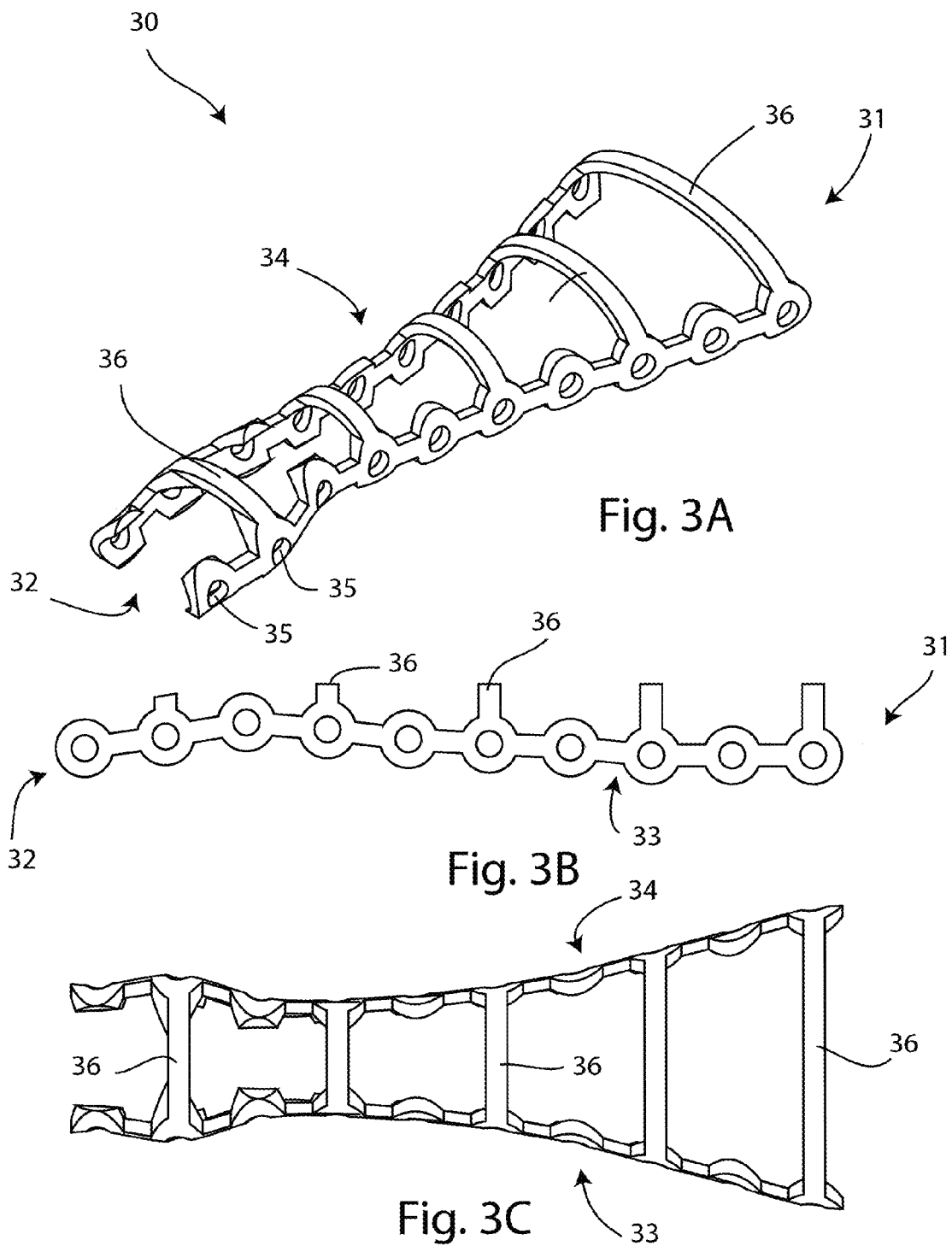

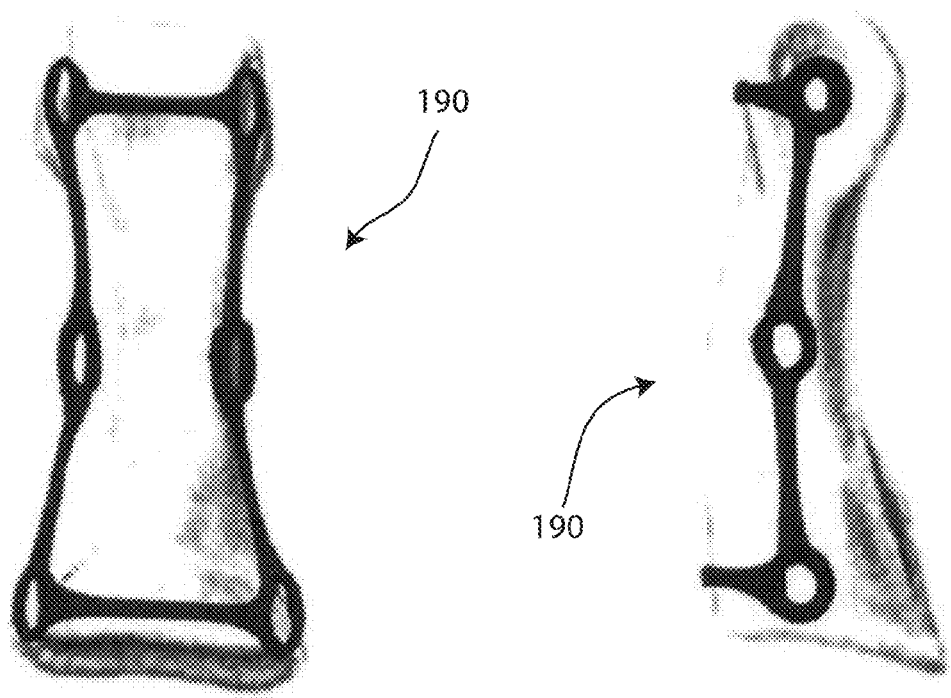
Fig. 19A
Fig. 19B
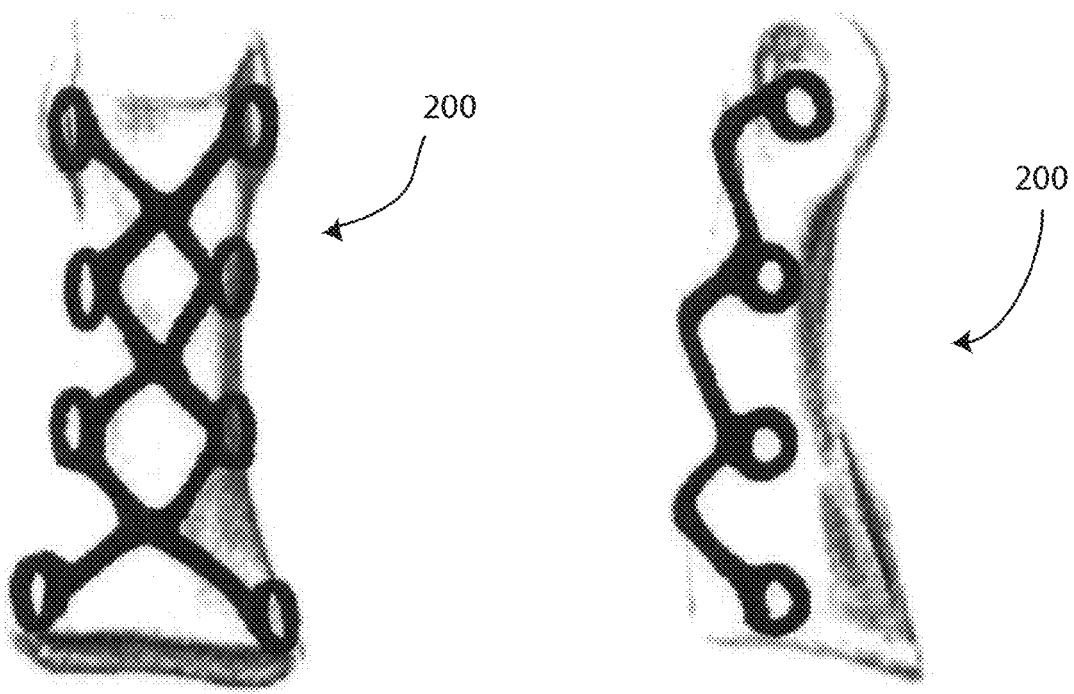
Fig. 20A
Fig. 20B

MODULAR BONE FIXATION SYSTEM

CROSS-REFERENCE TO RELATED APPLICATIONS

This application claims the benefit of:

U.S. Provisional Patent Application No. 61/583,527 which was filed Jan. 5, 2012, entitled: MODULAR BONE FIXATION SYSTEM.

The above-identified document is herein incorporated by reference in its entirety.

BACKGROUND

The present disclosure relates to implants, instruments and methods for repairing bones. More precisely, the present disclosure relates to an improved system for repairing fractures in bones, or otherwise stabilizing weak, diseased, or degenerative bones, including but not limited to bones of the hand or foot.

The implants, systems and methods disclosed herein provide many improvements over existing bone fixation technology including, but not limited to: implants that can provide inherent alignment, and stabilization forces to the bone; implants that can reduce the negative impact of the implant on the patient; and systems/methods which allow a single surgeon to surgically apply the implants to a patient.

In the treatment of various bone fractures, it is desirable to repair the fracture by aligning the bone fragments and stabilizing the bone fragments in the aligned position for a period of time sufficient to allow the bone fracture to heal. Restoring a fracture or dislocation to the correct alignment may also be referred to as "setting the bone", "reducing the fracture", or simply "reduction." Depending on the type of fracture, the bone fragments can be realigned utilizing either a "closed reduction" procedure or an "open reduction" procedure. A closed reduction procedure does not require surgical incisions to access the bone fragments to align them. Rather, the doctor can manipulate the bone fragments with his/her hands to align the bone fragments and then apply an external device, such as a cast, to stabilize the bone fragments while they heal. In contrast, an open reduction procedure involves surgically accessing the bone fragments to align and stabilize the bone fragments with implants such as bone plates or bone screws.

A wide variety of bone plates and screws have been developed in order to serve such purposes. Existing bone plate technology typically utilizes relatively thick bone plates in order to provide sufficient stabilization to the bone fragments. However, thicker bone plate implants increase the likelihood of irritation to the patient's surrounding soft tissues, causing inflammation, pain and other complications.

Moreover, existing bone plate and bone screw technology is typically applied to the patient by a team of surgeons. Usually, one surgeon will reduce the fracture and hold the bone fragments in place while the other surgeon attaches the thick bone plates to the bone fragments. Furthermore, existing bone fracture alignment tools can be cumbersome, complex, and bulky.

Therefore, it is desirable to provide a bone repair system that can simplify the surgical procedure by providing implants with inherent bone fragment alignment and stabilization characteristics; thinner implants to reduce the negative impact of the implants on the patient; and devices, systems, and methods which simplify the surgical procedure to allow a single surgeon to affix the implants to fractured bones.

Those of skill in the art will recognize that the following description is merely illustrative of the principles of the disclosure, which may be applied in various ways to provide many different alternative examples and may be applicable outside the fields of surgery or medical devices. It will be appreciated that various features of the examples and examples of the present disclosure may be mixed and matched to form a variety of other combinations and alternative examples without departing from the spirit or essential characteristics of the present disclosure. The scope of the present disclosure is, therefore, indicated by the appended claims rather than by the following examples and examples described herein. As such, the described examples are to be considered in all respects only as illustrative and not restrictive. While the present disclosure is made in the context of tubular hand bones for the purposes of illustrating the concepts of the design, it is contemplated that the present design and/or variations thereof may be suited to other bones, including but not limited to: foot bones, any tubular bone of any size or shape, or any non-tubular bone of any size or shape.

All changes which come within the meaning and range of equivalency of the claims are to be embraced within their scope.

Standard medical planes of reference and descriptive terminology are employed in this specification. A sagittal plane divides a body into right and left portions. A mid-sagittal plane divides the body into equal right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. These descriptive terms may be applied to an animate or inanimate body.

BRIEF DESCRIPTION OF THE DRAWINGS

Various examples of the present disclosure will now be discussed with reference to the appended drawings. It will be appreciated that these drawings depict only typical examples of the present disclosure and are therefore not to be considered limiting of its scope.

FIG. 2A is an isometric view of an implant in accordance with another example of the present disclosure;

FIG. 2B is a side view of the implant of FIG. 2A;

FIG. 2C is a top view of the implant of FIG. 2A;

FIG. 3A is an isometric view of an implant in accordance with another example of the present disclosure;

FIG. 3B is a side view of the implant of FIG. 3A;

FIG. 3C is a top view of the implant of FIG. 3A;

FIG. 19A is a top view of an implant attached to a tubular bone in accordance with another example of the present disclosure;
FIG. 19B is a side view of the implant of FIG. 19A;
FIG. 20A is a top view of an implant attached to a tubular bone in accordance with another example of the present disclosure;
FIG. 20B is a side view of the implant of FIG. 20A.

DETAILED DESCRIPTION

Figure 1A:
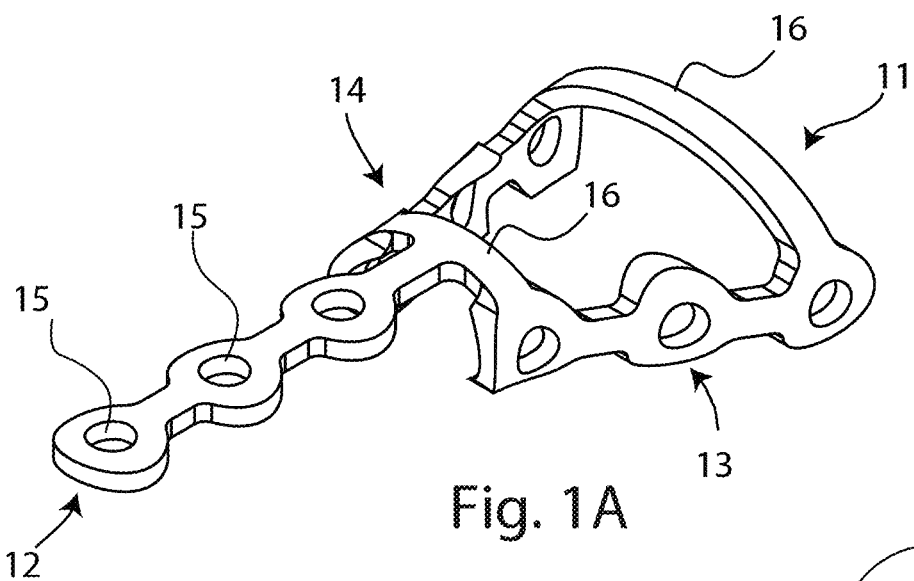
FIG. 1A is an isometric view of an implant in accordance with one example of the present disclosure.

While certain examples are shown and described in detail below by way of illustration only, it will be clear to the person skilled in the art upon reading and understanding this disclosure that changes, modifications, and variations may be made and remain within the scope of the technology described herein. Furthermore, while various features are grouped together in the examples for the purpose of streamlining the disclosure, it is appreciated that features from different examples may be combined to form additional examples which are all contemplated within the scope of the disclosed technology.

Not every feature of each example is labeled in every figure in which that example appears, in order to keep the figures clear. Similar reference numbers (for example, those that are identical except for the first numeral) may be used to indicate similar features in different examples.

Any of the devices described herein may be fabricated from metals, alloys, polymers, plastics, ceramics, glasses, composite materials, or combinations thereof, including but not limited to: PEEK, titanium, titanium alloys, commercially pure titanium grade 2 per ASTM Standard ASTM F-67, Titanium-6 Aluminum-4 Vanadium titanium alloy per ASTM Standard F-136, Nitinol, cobalt chrome, stainless steel, UHMWPE, and biodegradable materials, among others. Different materials may be used within a single part. The implants disclosed herein may also encompass a variety of surface treatments to encourage bony attachment such as porous coatings, hydroxyapatite, and TCP, among others. Any implant disclosed herein may include a radiographic marker for imaging purposes.

Each of the implants disclosed herein can be pre-formed or additionally shaped during surgery to anatomically "cup" or "wrap" around the bone to aid in initial reduction of the fracture and to hold bone fragments in place while the surgeon fixes the implant to the bone fragments.

Each of the implants disclosed herein can be cut to fit the specific anatomy of the patient to achieve better anatomic specificity; reduce the number of implants necessary for a given surgical kit of implants; and to allow the surgeon to save any "left over" (non-implanted) portion of the implants to be returned to the kit for use at a future date.

Each of the implants disclosed herein can have variable hole configurations that can be adapted to correspond to varying bone morphology. For example, in areas where larger diameter screws could be accommodated by the bone morphology, larger screw holes can be placed in the plates allowing for optimal screw sizes to be used in specific anatomical areas to provide optimal fixation and strength.

Each of the implants disclosed herein can have regions of variable thickness to correspond to different bone morphology. For example, the variable thickness regions may correspond to the portions of the plates used to accommodate larger screw diameters allowing for optimal screw size and plate thickness to be used in specific anatomical areas to provide optimal fixation and strength.

Each of the implants disclosed herein can have geometries that are offered with both parallel and convergent hole configurations to allow for optimal anatomic specificity of the implant. For example, in a bone that varies in diameter between the proximal and distal ends of the bone, a plate with convergent holes may be preferable to better fit the anatomy of the bone. Additionally, convergent holes in the plates can provide better reduction forces to the fracture in some examples.

Each of the implants disclosed herein can utilize one or more bridging screws to connect portions of the implant on contra-lateral sides to each other through the bridging screw. This feature can provide additional compression and reduction forces between portions of the implant. Some examples may include the ability to lock the screw to the contra-lateral side of the device through threads or some other mechanism built into the device. Other examples may include the ability to lock the screw to the contra-lateral side of the device through a bolt and nut configuration where the distal end of the screw passes through the contra-lateral hole in the plate and then an additional component (e.g. a nut) is used to affix the screw to the plate.

Some implants disclosed herein can have at least one third portion that is configured to rise above the extensor (or flexor) tendon and be removed after the implant is attached to the bone.

Some implants disclosed herein can have scored surfaces at or near the junctions where the at least one third portion connects to the first portion and the second portion. Once the implant is attached to the bone, the surgeon can cut the at least one third portion into two pieces at or near the apex of the at least one third portion and bend each piece of the at least one third portion until it cleanly breaks away from the first or second portion at or near the scored surfaces.

Figure 7A:
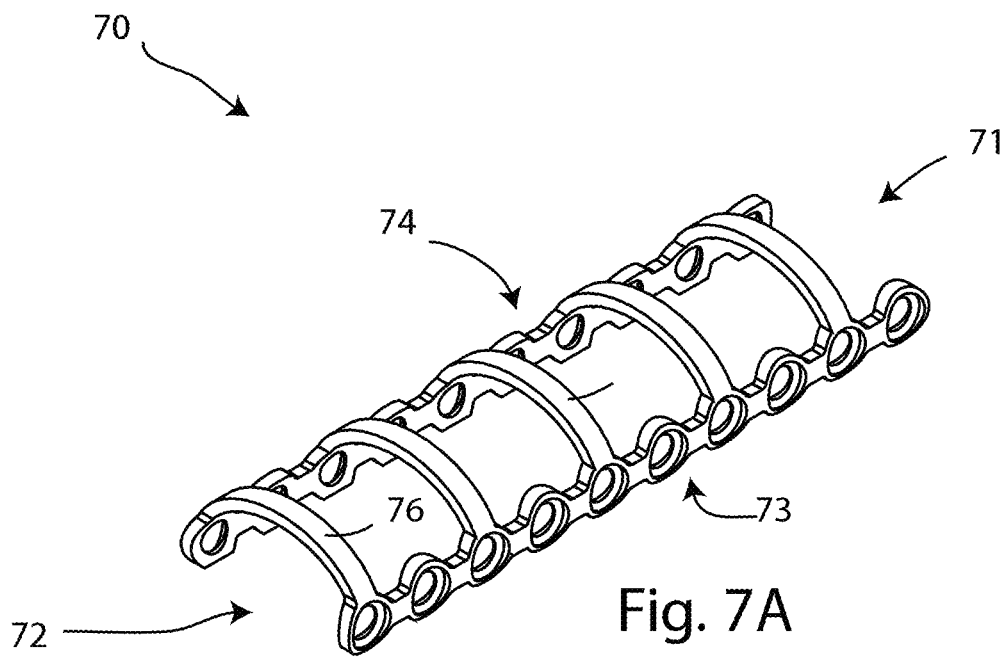
FIG. 7A is an isometric view of an implant in accordance with another example of the present disclosure.
Figure 7B:
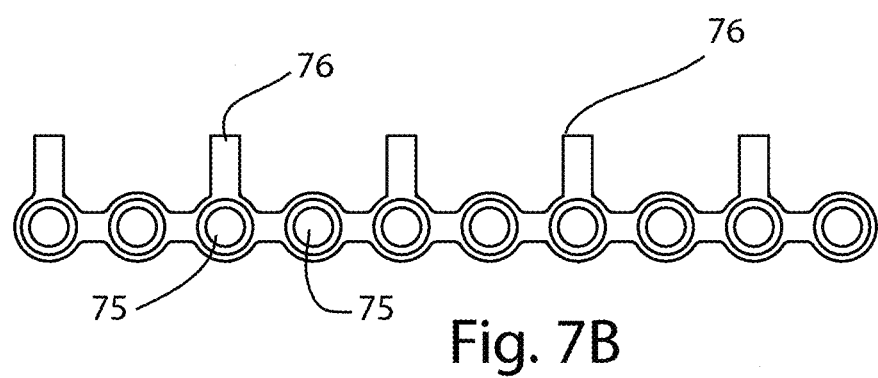
FIG. 7B is a side view of the implant of FIG. 7A.
Figure 7C:
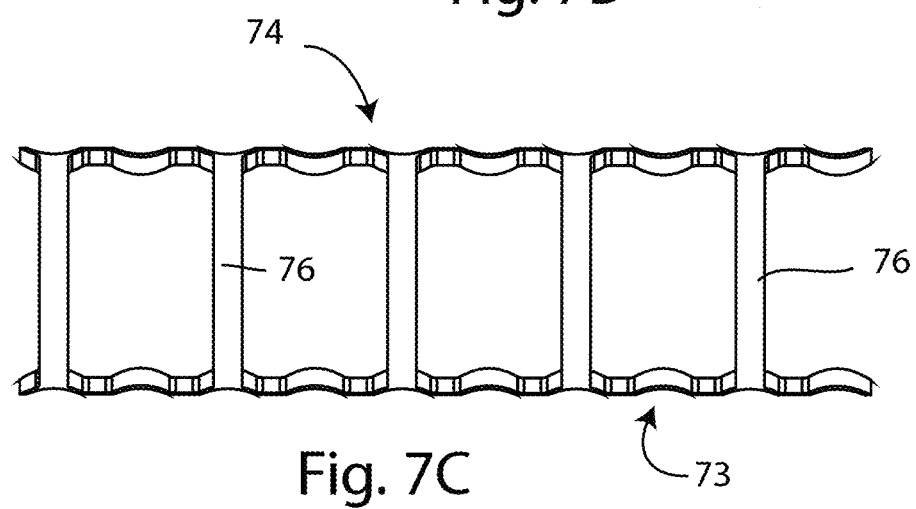
FIG. 7C is a top view of the implant of FIG. 7A.
Figure 8:
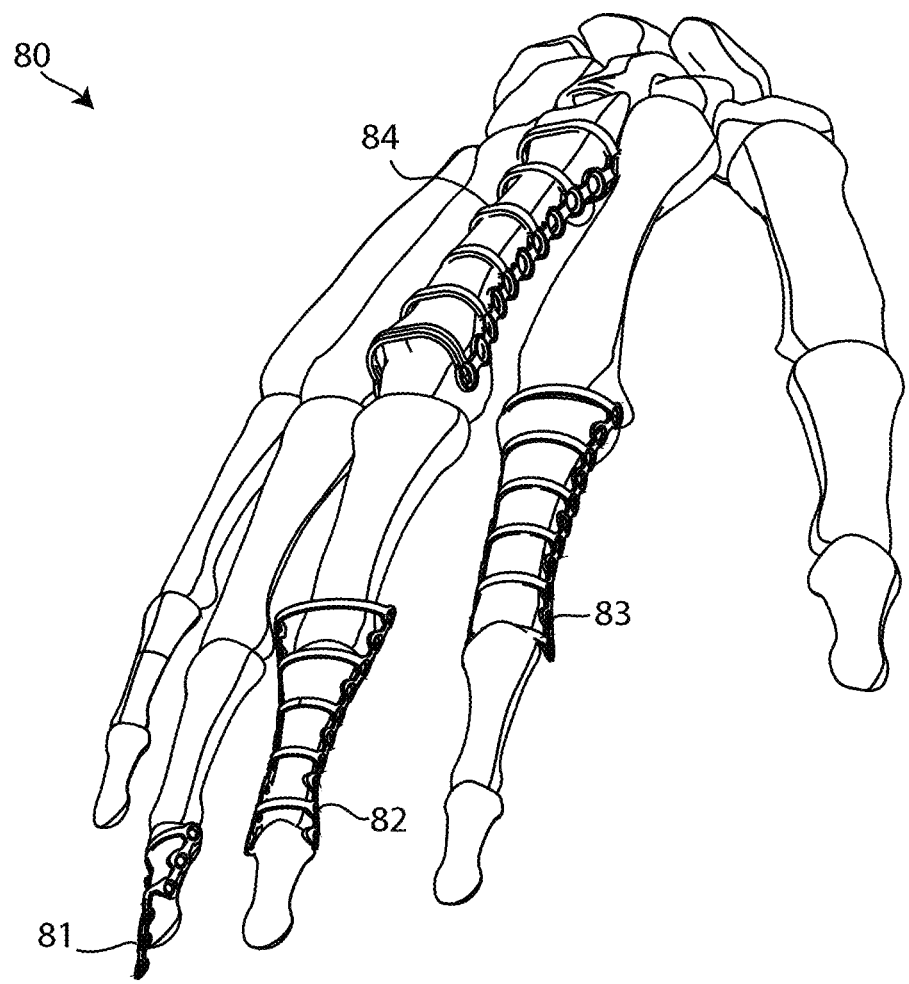
FIG. 8 is an isometric view of hand bones with various implants sized and shaped to attach to different bones of the hand.
Figure 9A:
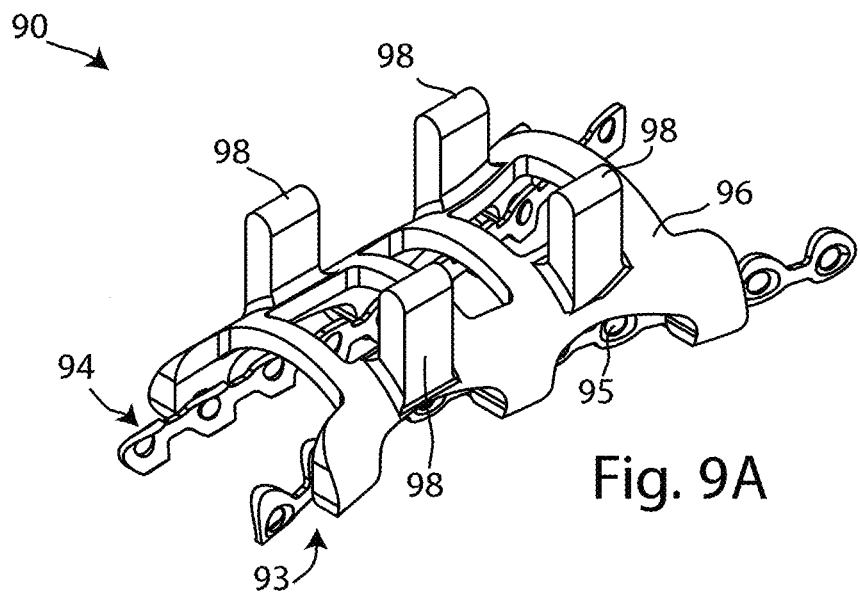
FIG. 9A is an isometric view of an implant system in accordance with another example of the present disclosure.
Figure 9B:
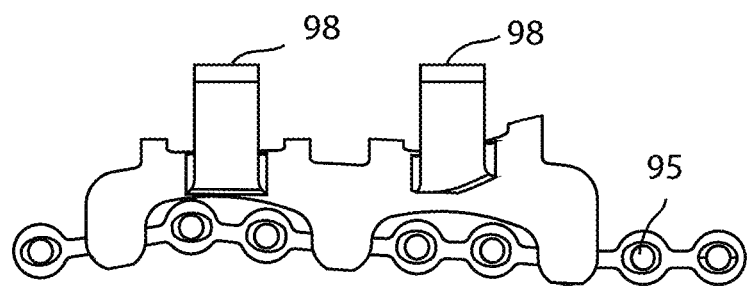
FIG. 9B is a side view of the implant system of FIG. 9A.
Figure 9C:
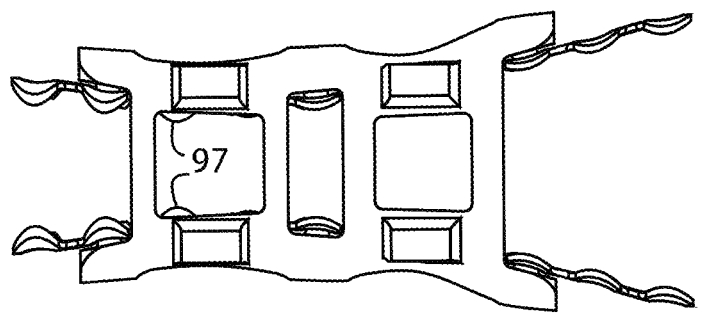
FIG. 9C is a top view of the implant system of FIG. 9A.
Figure 9D:
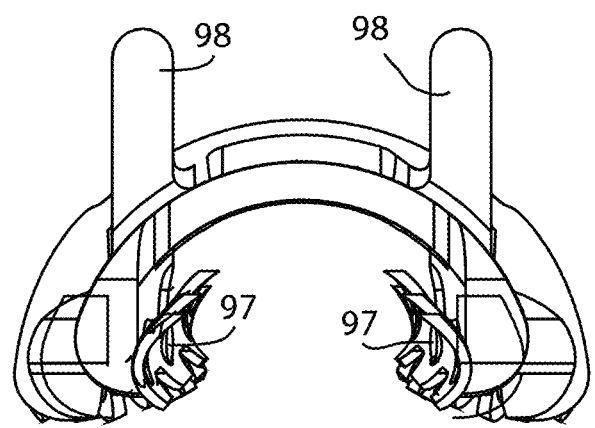
FIG. 9D is a front view of the implant system of FIG. 9A.
Figure 9E:
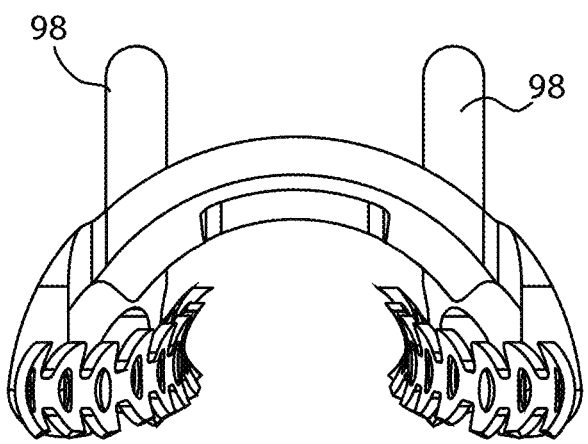
FIG. 9E is a back view of the implant system of FIG. 9A.
Figure 9F:
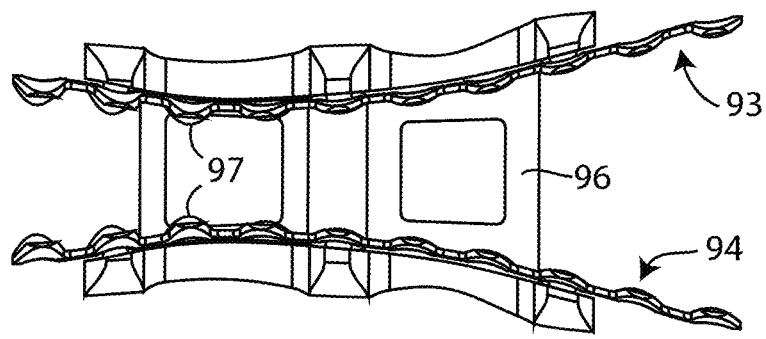
FIG. 9F is a bottom view of the implant system of FIG. 9A.

FIGS. 1A-8 illustrate various embodiments of implants with different sizes and shapes, each configured to conform to the various anatomic shapes of different bones. FIG. 8 shows how different implants can be utilized to anatomically repair fractures in the various bones of a human hand.

Figure 1B:
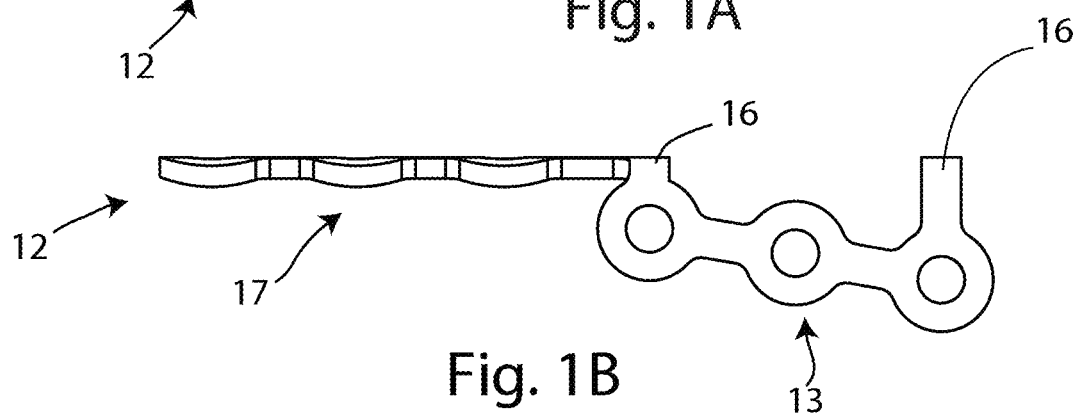
FIG. 1B is a side view of the implant of FIG. 1A.
Figure 1C:
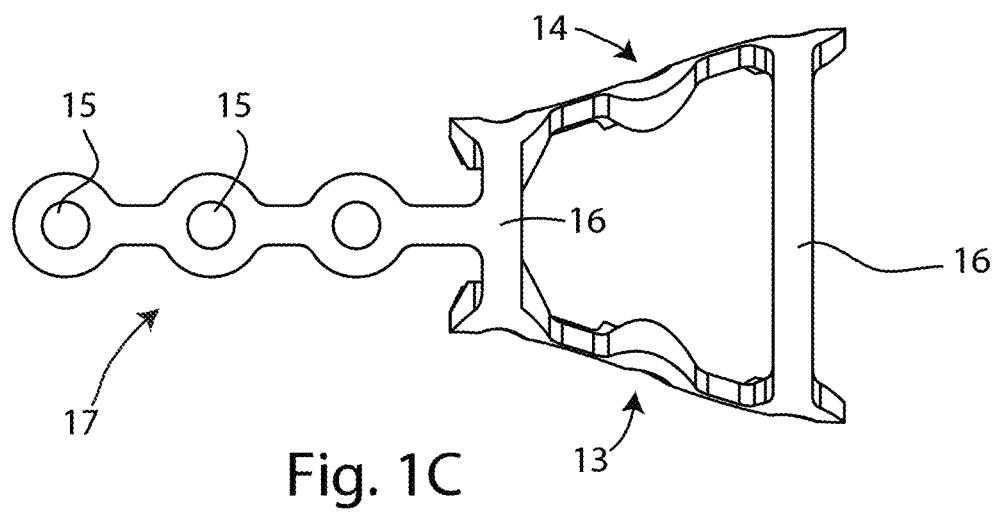
FIG. 1C is a top view of the implant of FIG. 1A.

FIGS. 1A-1C show an implant 10 sized and shaped to reduce fractures in small distal phalanges. The implant 10 has a proximal end 11 and a distal end 12. The implant 10 also has a first portion 13 and a second portion 14 contralateral to each other. The implant 10 may also include at least one third portion 16, intermediate and substantially transverse the first portion 13 and the second portion 14, configured to aid in aligning and holding bone fragments while a surgeon affixes the implant to a bone placed between the first portion 13 and the second portion 14. The implant 10 may also include a protrusion 17 extending distally from at least one of the third portion 16 and terminating at the distal end 12. The implant 10 may have one or more apertures 15 which extend entirely through the implant and are configured to receive one or more attachment devices (not shown), such as bone screws, to fixedly attached the implant 10 to the bone.

In one example, the at least one third portion 16 is configured to lie below the flexor or extensor tendons, while the first portion 13 and the second portion 14 engage surfaces of the bone to the sides of the flexor and extensor tendons. In this configuration, the first portion 13 and the second portion 14 act synergistically to provide better stabilization to the bone which allows the thickness of the implant 10 to be much less than it would otherwise need to be. In some examples the thickness of the implant 10 can be about 0.38 mm thick. In other examples, the thickness of the implant 10 can be less than 0.38 mm thick. In yet other examples, the thickness of the implant 10 can be between about 0.38 mm and 1.2 mm thick. In still other examples, the thickness of the implant can vary throughout the length of the implant. For example, in some embodiments the thickness of the implant can decrease in the proximal to distal direction. Reducing the thickness of the implant 10 reduces the irritation to the patient's soft tissues above the bone, including but not limited to any extensor or flexor tendons that may lie above the at least one third portion 16.

Figure 12A:
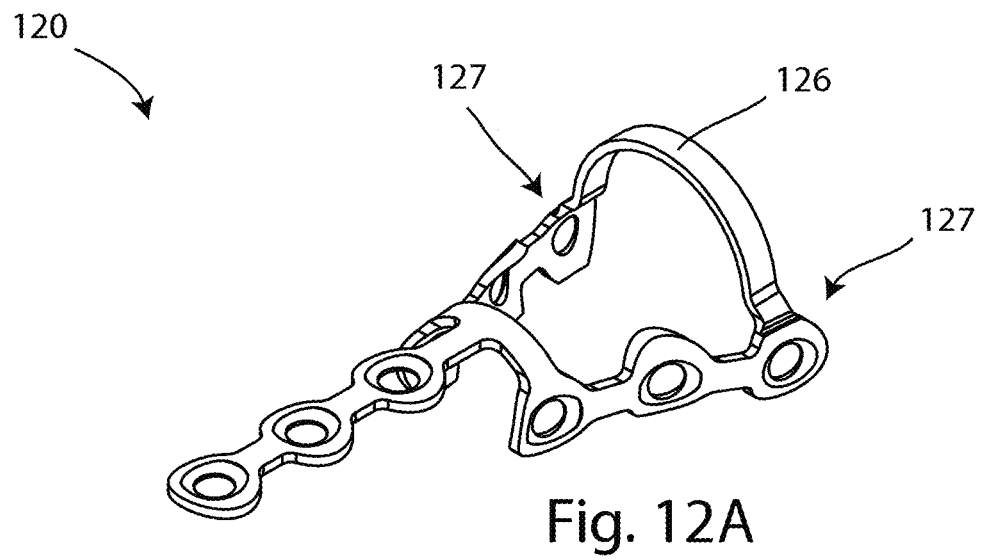
FIG. 12A is an isometric view of an implant in accordance with another example of the present disclosure.
Figure 12B:
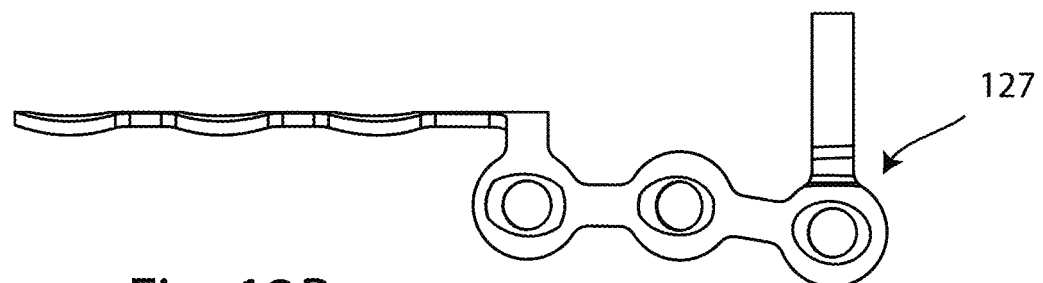
FIG. 12B is a side view of the implant of FIG. 12A.
Figure 12C:
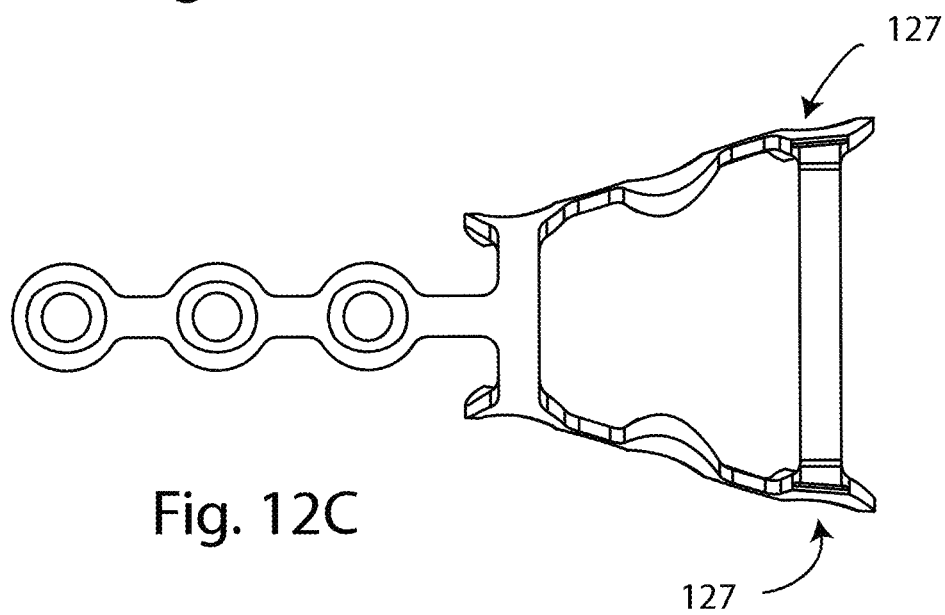
FIG. 12C is a top view of the implant of FIG. 12A.

FIGS. 12A-12C show an alternative implant 120 sized and shaped to reduce fractures in small distal phalanges similar in some respects to that shown in FIGS. 1A-1C. However, the implant 120 shown in FIGS. 12A-12C has at least one third portion 126 which is configured to lie above the extensor or flexor tendon. The implant 120 can also have scored surfaces 127 intermediate the at least one third portion 126 and the first and second portions. This example allows the surgeon to affix the implant 120 to the bone with the at least one third portion 126 over the flexor or extensor tendon. Thus, the surgeon does not have to retract the tendon to one side in order to place the implant around the bone. Once the surgeon affixes the implant 120 to the bone, the surgeon can remove the at least one third portion by bending the at least one third portion relative to the first and second portions to break away the at least one third portion at or near the scored surfaces 127.

FIGS. 2A-2C show an implant 20 sized and shaped to reduce fractures in larger distal phalanges. The implant 20 has a proximal end 21 and a distal end 22. The implant 20 also has a first portion 23 and a second portion 24 contralateral to each other. The implant 20 may have one or more apertures 25 configured to receive one or more attachment devices (not shown), such as bone screws, to fixedly attached the implant 20 to the bone. The implant 20 may also include at least one third portion 26, intermediate and substantially transverse the first portion 23 and the second portion 24, configured to aid in aligning and holding bone fragments while a surgeon affixes the implant to a bone placed between the first portion 23 and the second portion 24. The implant 20 may also include a protrusion 27 extending distally from at least one of the third portion 26 and terminating at the distal end 22. The implant 20 may have one or more apertures 25 which extend entirely through the implant and are configured to receive one or more attachment devices (not shown), such as bone screws, to fixedly attached the implant 20 to the bone.

In one example, the at least one third portion 26 is configured to lie below the flexor or extensor tendons, while the first portion 23 and the second portion 24 engage surfaces of the bone to the sides of the flexor and extensor tendons. In this configuration, the first portion 23 and the second portion 24 act synergistically to provide better stabilization to the bone which allows the thickness of the implant 20 to be much less than it would otherwise need to be. In some examples the thickness of the implant 20 can be about 0.38 mm thick. In other examples, the thickness of the implant 20 can be less than 0.38 mm thick. In yet other examples, the thickness of the implant 20 can be between about 0.38 mm and 1.2 mm thick. Reducing the thickness of the implant 20 reduces the irritation to the patient's soft tissues above the bone including extensor or flexor tendons that may lie above the at least one third portion 26.

Figure 13A:
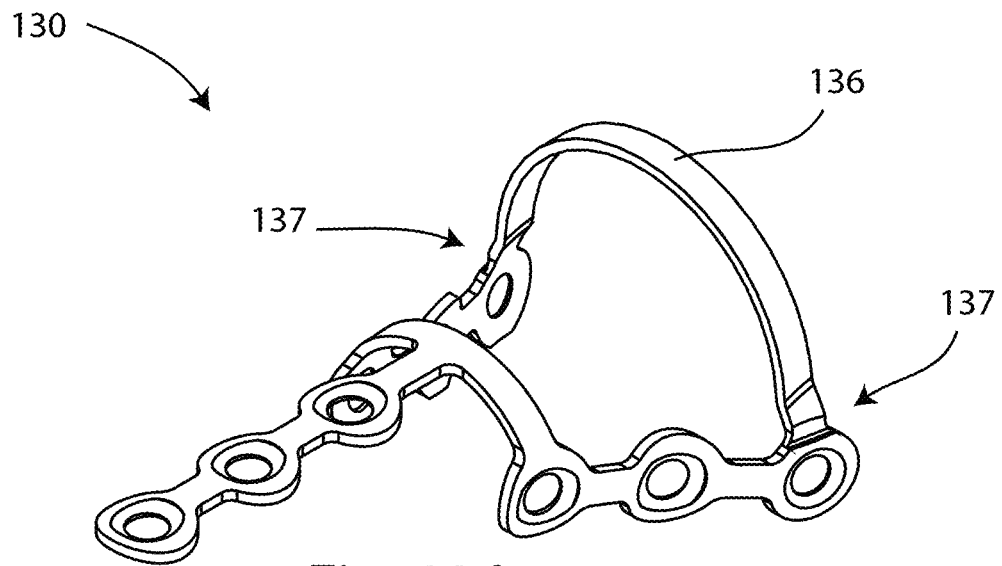
FIG. 13A is an isometric view of an implant in accordance with another example of the present disclosure.
Figure 13B:
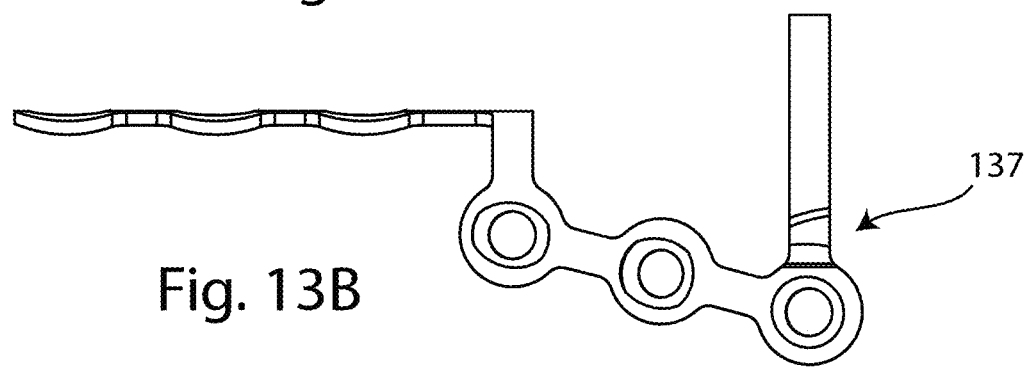
FIG. 13B is a side view of the implant of FIG. 13A.
Figure 13C:
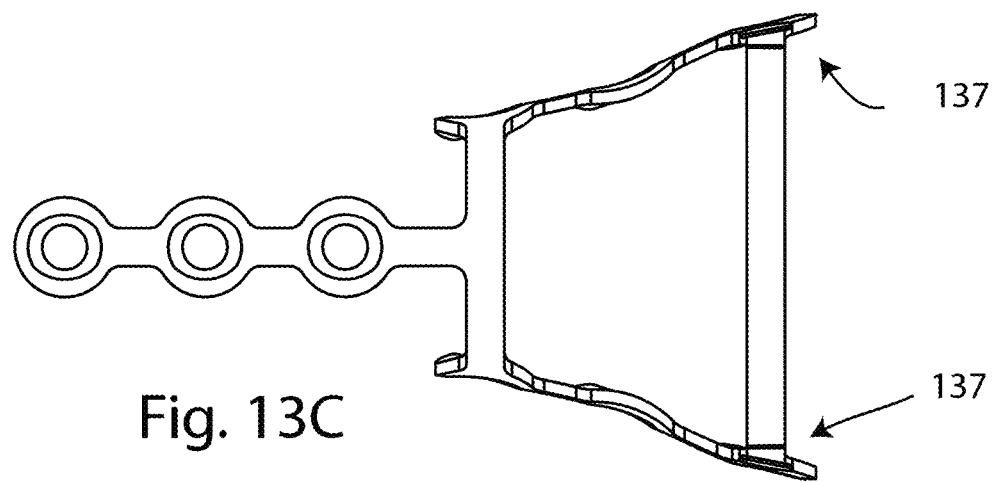
FIG. 13C is a top view of the implant of FIG. 13A.

FIGS. 13A-13C show an alternative implant 130 sized and shaped to reduce fractures in larger distal phalanges similar in some respects to that shown in FIGS. 2A-2C. However, the implant 130 shown in FIGS. 13A-13C has at least one third portion 136 which is configured to lie above the flexor or extensor tendon. The implant 130 can also have scored surfaces 137 intermediate the at least one third portion 136 and the first and second portions. This example allows the surgeon to affix the implant 130 to the bone with the at least one third portion 136 over the flexor or extensor tendon. Thus, the surgeon does not have to retract the tendon to one side in order to place the implant around the bone. Once the surgeon affixes the implant 130 to the bone, the surgeon can remove the at least one third portion by bending the at least one third portion relative to the first and second portions to break away the at least one third portion at or near the scored surfaces 137.

FIGS. 3A-3C show an implant 30 sized and shaped to reduce fractures in small middle phalanges. The implant 30 has a proximal end 31 and a distal end 32. The implant 30 also has a first portion 33 and a second portion 34 contralateral to each other. The implant 30 may have one or more apertures 35 configured to receive one or more attachment devices (not shown), such as bone screws, to fixedly attached the implant 30 to the bone. The implant 30 may also include at least one third portion 36, intermediate and substantially transverse the first portion 33 and the second portion 34, configured to aid in aligning and holding bone fragments while a surgeon affixes the implant to a bone placed between the first portion 33 and the second portion 34. From a top view the implant 30 may resemble an hour-glass shape. The implant 30 may also resemble a ladder shape.

In one example, the at least one third portion 36 is configured to lie below the flexor or extensor tendons, while the first portion 33 and the second portion 34 engage surfaces of the bone to the sides of the flexor and extensor tendons. In this configuration, the first portion 33 and the second portion 34 act synergistically to provide better stabilization to the bone which allows the thickness of the implant 30 to be much less than it would otherwise need to be. In some examples the thickness of the implant 30 can be about 0.38 mm thick. In other examples, the thickness of the implant 30 can be less than 0.38 mm thick. In yet other examples, the thickness of the implant 30 can be between about 0.38 mm and 1.2 mm thick. Reducing the thickness of the implant 30 reduces the irritation to the patient's soft tissues above the bone including extensor or flexor tendons that may lie above the at least one third portion 36.

Figure 14A:
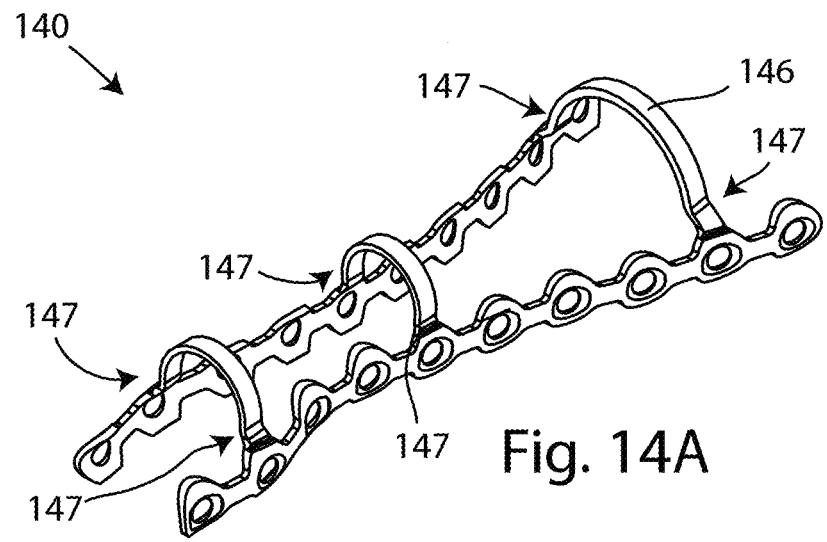
FIG. 14A is an isometric view of an implant in accordance with another example of the present disclosure.
Figure 14B:
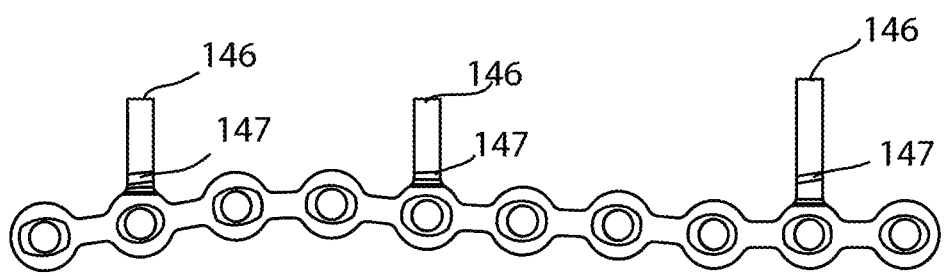
FIG. 14B is a side view of the implant of FIG. 14A.
Figure 14C:
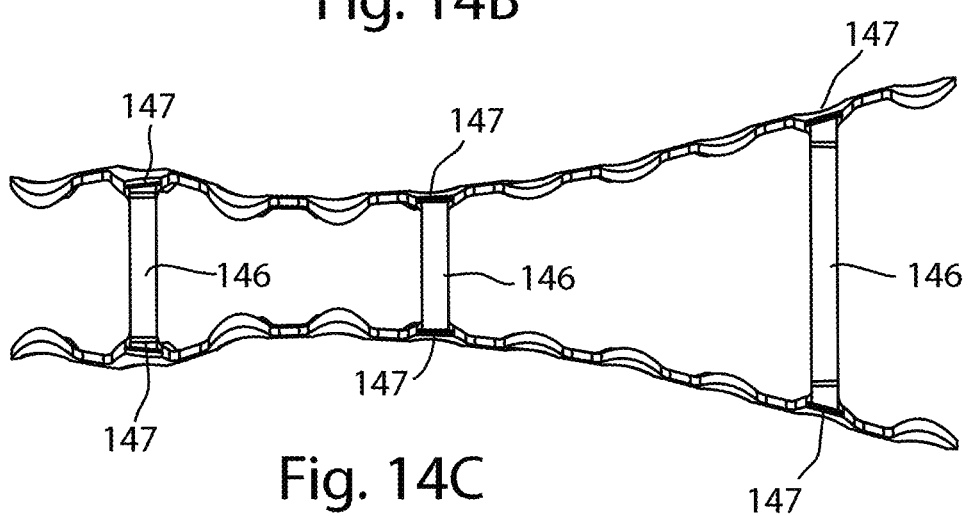
FIG. 14C is a top view of the implant of FIG. 14A.

FIGS. 14A-14C show an alternative implant 140 sized and shaped to reduce fractures in small middle phalanges similar in some respects to that shown in FIGS. 3A-3C. However, the implant 140 shown in FIGS. 14A-14C has at least one third portion 146 which is configured to lie above the flexor or extensor tendon. The implant 140 can also have scored surfaces 147 intermediate the at least one third portion 146 and the first and second portions. This example allows the surgeon to affix the implant 140 to the bone with the at least one third portion 146 over the flexor or extensor tendon. Thus, the surgeon does not have to retract the tendon to one side in order to place the implant around the bone. Once the surgeon affixes the implant 140 to the bone, the surgeon can remove the at least one third portion by bending the at least one third portion relative to the first and second portions to break away the at least one third portion at or near the scored surfaces 147.

Figure 4A:
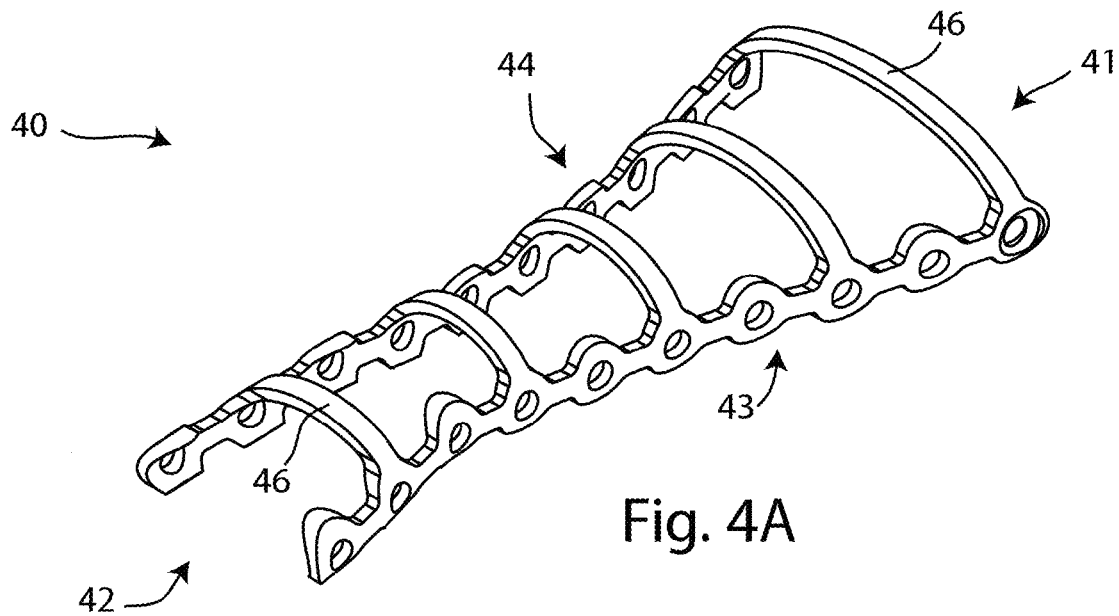
FIG. 4A is an isometric view of an implant in accordance with another example of the present disclosure.
Figure 4B:
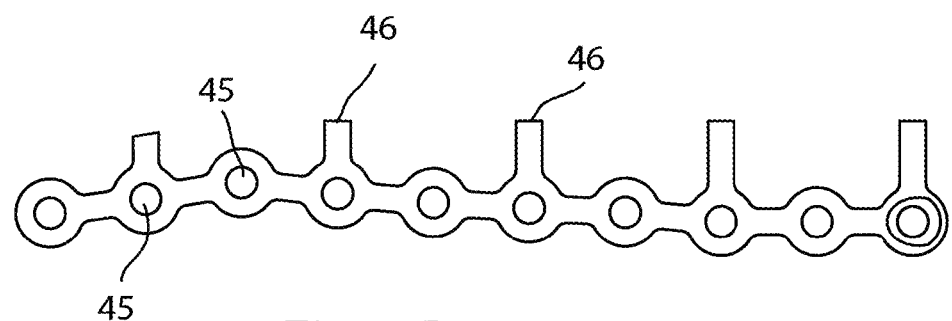
FIG. 4B is a side view of the implant of FIG. 4A.
Figure 4C:
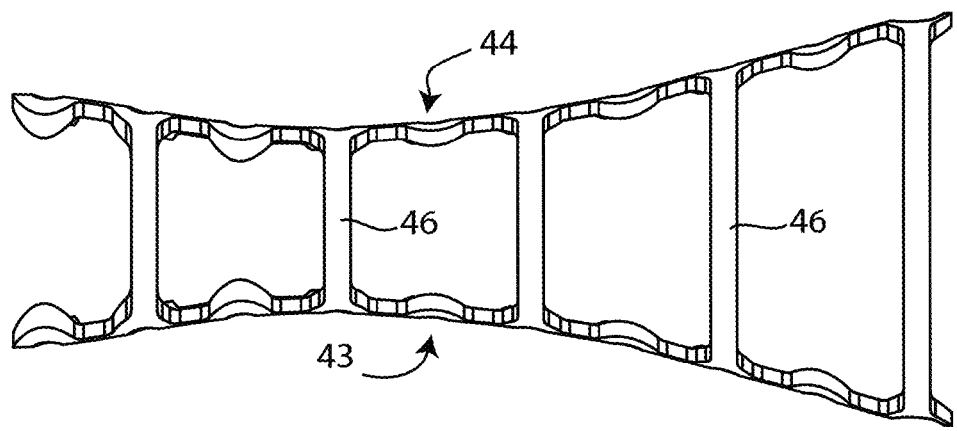
FIG. 4C is a top view of the implant of FIG. 4A.

FIGS. 4A-4C show an implant 40 sized and shaped to reduce fractures in large middle phalanges. The implant 40 has a proximal end 41 and a distal end 42. The implant 40 also has a first portion 43 and a second portion 44 contralateral to each other. The implant 40 may have one or more apertures 45 configured to receive one or more attachment devices (not shown), such as bone screws, to fixedly attached the implant 40 to the bone. The implant 40 may also include at least one third portion 46, intermediate and substantially transverse the first portion 43 and the second portion 44, configured to aid in aligning and holding bone fragments while a surgeon affixes the implant to a bone placed between the first portion 43 and the second portion 44. From a top view the implant 40 may resemble an hour-glass shape. The implant 40 may also resemble a ladder shape.

In one example, the at least one third portion 46 is configured to lie below the flexor or extensor tendons, while the first portion 43 and the second portion 44 engage surfaces of the bone to the sides of the flexor and extensor tendons. In this configuration, the first portion 43 and the second portion 44 act synergistically to provide better stabilization to the bone which allows the thickness of the implant 40 to be much less than it would otherwise need to be. In some examples the thickness of the implant 40 can be about 0.38 mm thick. In other examples, the thickness of the implant 40 can be less than 0.38 mm thick. In yet other examples, the thickness of the implant 40 can be between about 0.38 mm and 1.2 mm thick. Reducing the thickness of the implant 40 reduces the irritation to the patient's soft tissues above the bone including extensor or flexor tendons that may lie above the at least one third portion 46.

Figure 15A:
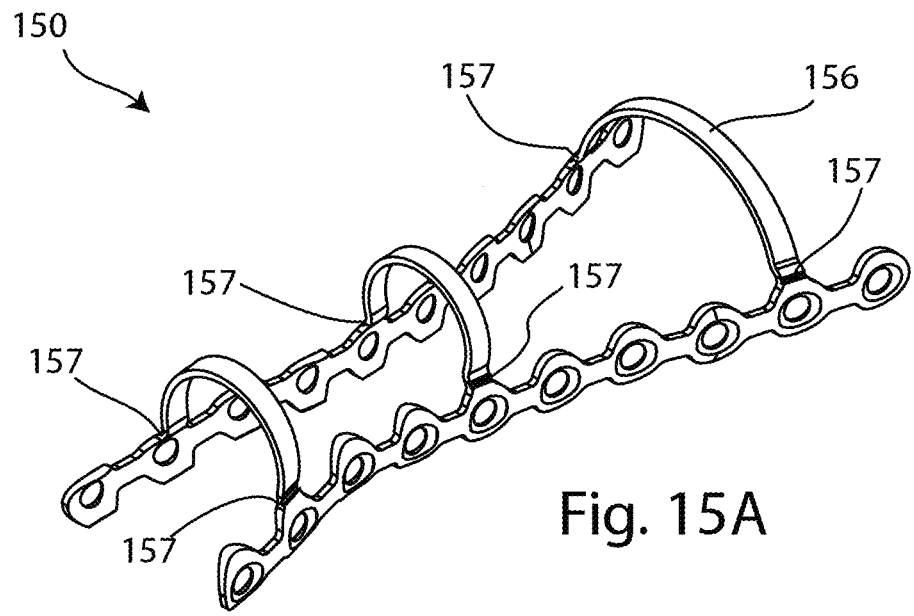
FIG. 15A is an isometric view of an implant in accordance with another example of the present disclosure.
Figure 15B:
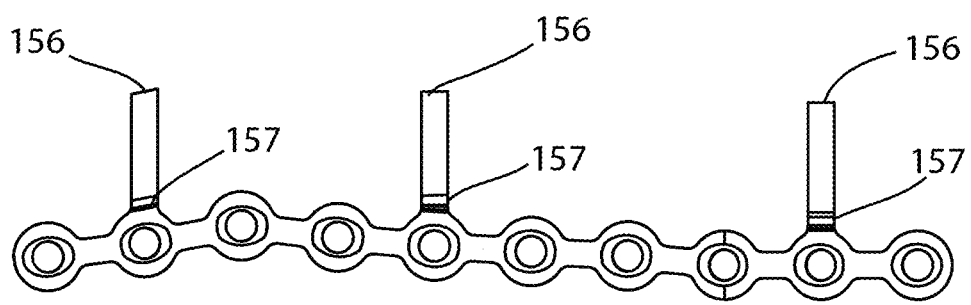
FIG. 15B is a side view of the implant of FIG. 15A.
Figure 15C:
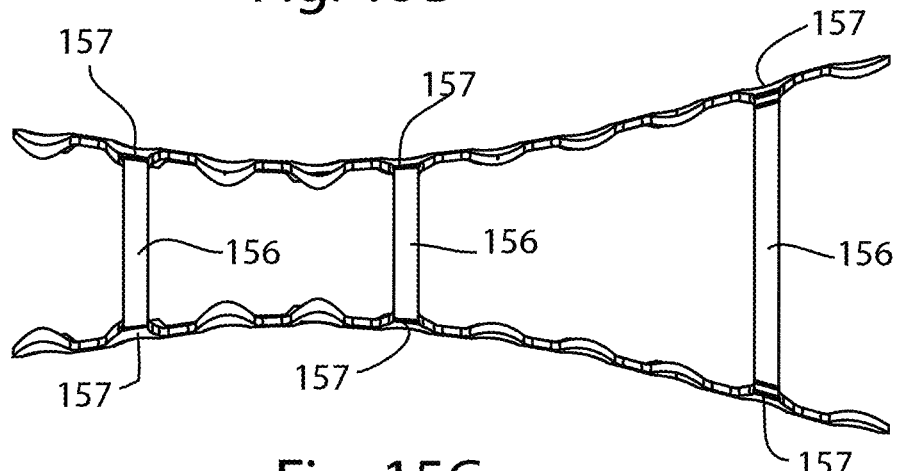
FIG. 15C is a top view of the implant of FIG. 15A.

FIGS. 15A-15C show an alternative implant 150 sized and shaped to reduce fractures in large middle phalanges similar in some respects to that shown in FIGS. 4A-4C. However, the implant 150 shown in FIGS. 15A-15C has at least one third portion 156 which is configured to lie above the flexor or extensor tendon. The implant 150 can also have scored surfaces 157 intermediate the at least one third portion 156 and the first and second portions. This example allows the surgeon to affix the implant 150 to the bone with the at least one third portion 156 over the flexor or extensor tendon. Thus, the surgeon does not have to retract the tendon to one side in order to place the implant around the bone. Once the surgeon affixes the implant 150 to the bone, the surgeon can remove the at least one third portion by bending the at least one third portion relative to the first and second portions to break away the at least one third portion at or near the scored surfaces 157.

Figure 5A:
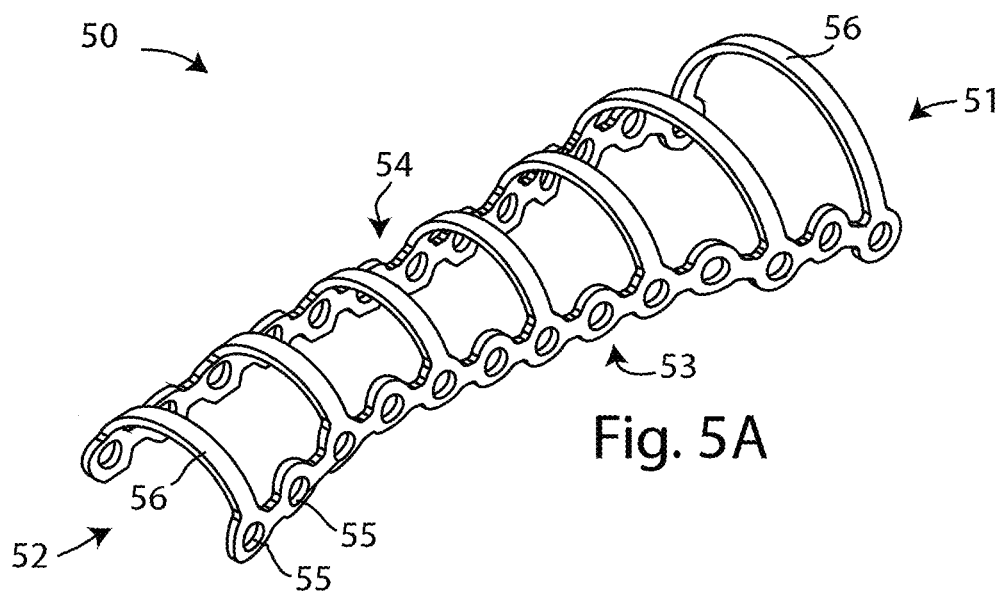
FIG. 5A is an isometric view of an implant in accordance with another example of the present disclosure.
Figure 5B:
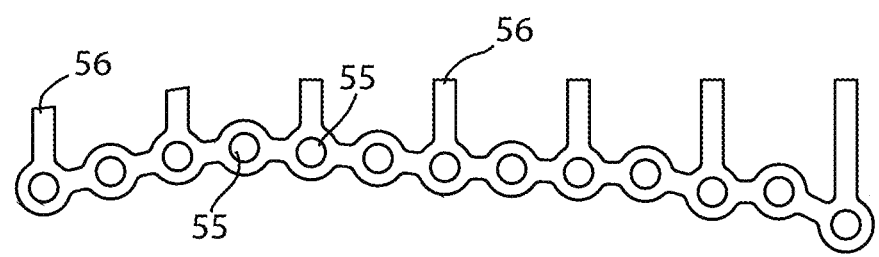
FIG. 5B is a side view of the implant of FIG. 5A.
Figure 5C:
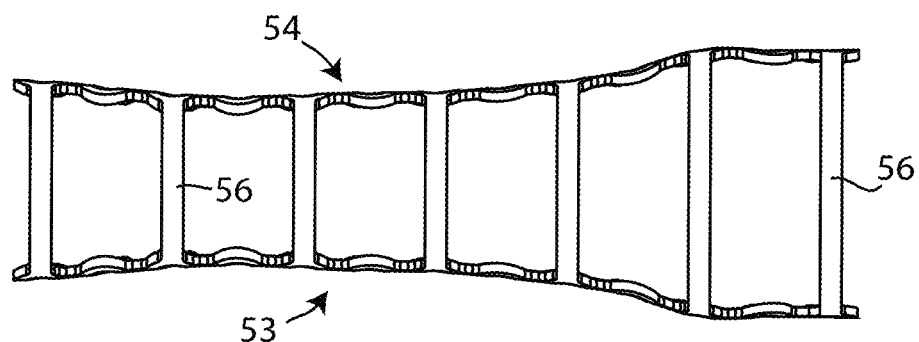
FIG. 5C is a top view of the implant of FIG. 5A.

FIGS. 5A-5C show an implant 50 sized and shaped to reduce fractures in proximal phalanges. The implant 50 has a proximal end 51 and a distal end 52. The implant 50 also has a first portion 53 and a second portion 54 contralateral to each other. The implant 50 may have one or more apertures 55 configured to receive one or more attachment devices (not shown), such as bone screws, to fixedly attached the implant 50 to the bone. The implant 50 may also include at least one third portion 56, intermediate and substantially transverse the first portion 53 and the second portion 54, configured to aid in aligning and holding bone fragments while a surgeon affixes the implant to a bone placed between the first portion 53 and the second portion 54. From a top view the implant 50 may resemble an hour-glass shape. The implant 50 may also resemble a ladder shape.

In one example, the at least one third portion 56 is configured to lie below the flexor or extensor tendons, while the first portion 53 and the second portion 54 engage surfaces of the bone to the sides of the flexor and extensor tendons. In this configuration, the first portion 53 and the second portion 54 act synergistically to provide better stabilization to the bone which allows the thickness of the implant 50 to be much less than it would otherwise need to be. In some examples the thickness of the implant 50 can be about 0.46 mm thick. In other examples, the thickness of the implant 50 can be less than 0.46 mm thick. In yet other examples, the thickness of the implant 50 can be between about 0.46 mm and 1.7 mm thick. Reducing the thickness of the implant 50 reduces the irritation to the patient's soft tissues above the bone including extensor or flexor tendons that may lie above the at least one third portion 56.

Figure 16A:
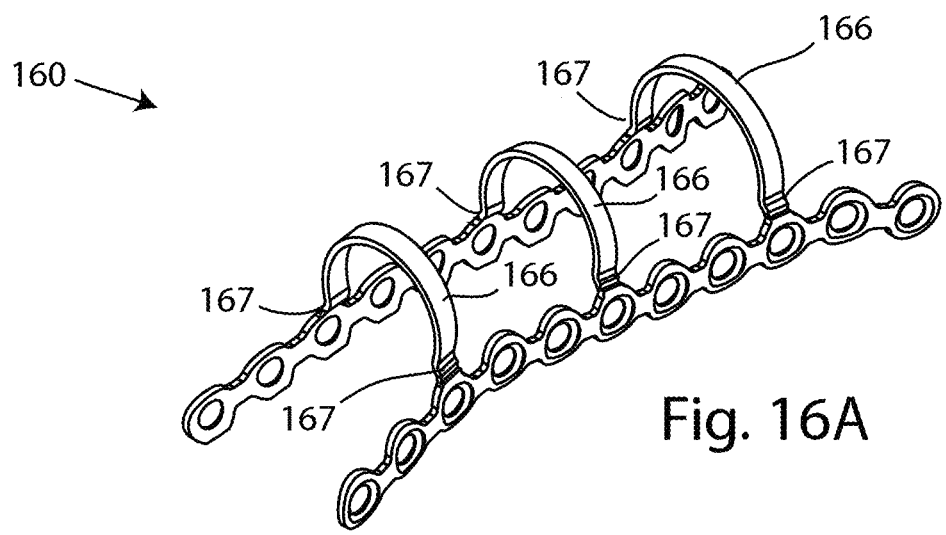
FIG. 16A is an isometric view of an implant in accordance with another example of the present disclosure.
Figure 16B:
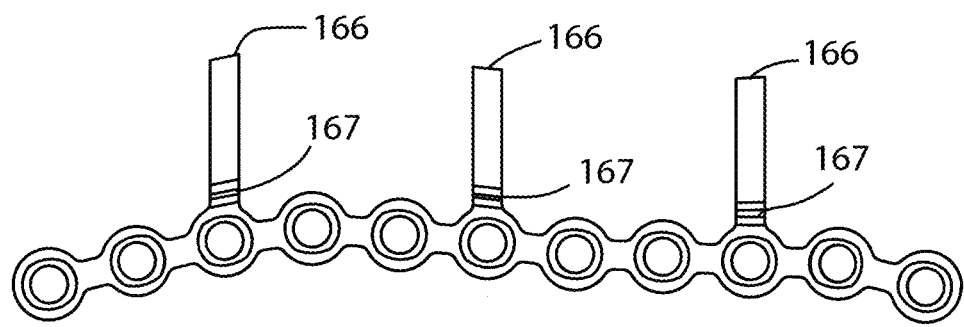
FIG. 16B is a side view of the implant of FIG. 16A.
Figure 16C:
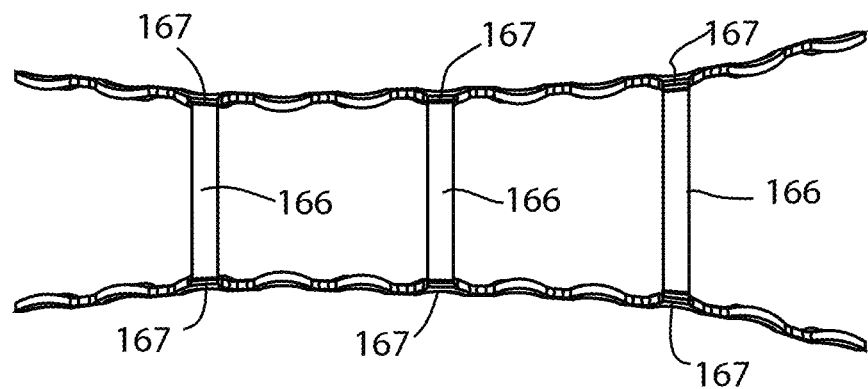
FIG. 16C is a top view of the implant of FIG. 16A.

FIGS. 16A-16C show an alternative implant 160 sized and shaped to reduce fractures in proximal phalanges similar in some respects to that shown in FIGS. 5A-5C. However, the implant 160 shown in FIGS. 16A-16C has at least one third portion 166 which is configured to lie above the flexor or extensor tendon. The implant 160 can also have scored surfaces 167 intermediate the at least one third portion 166 and the first and second portions. This example allows the surgeon to affix the implant 160 to the bone with the at least one third portion 166 over the flexor or extensor tendon. Thus, the surgeon does not have to retract the tendon to one side in order to place the implant around the bone. Once the surgeon affixes the implant 160 to the bone, the surgeon can remove the at least one third portion by bending the at least one third portion relative to the first and second portions to break away the at least one third portion at or near the scored surfaces 167.

Figure 6A:
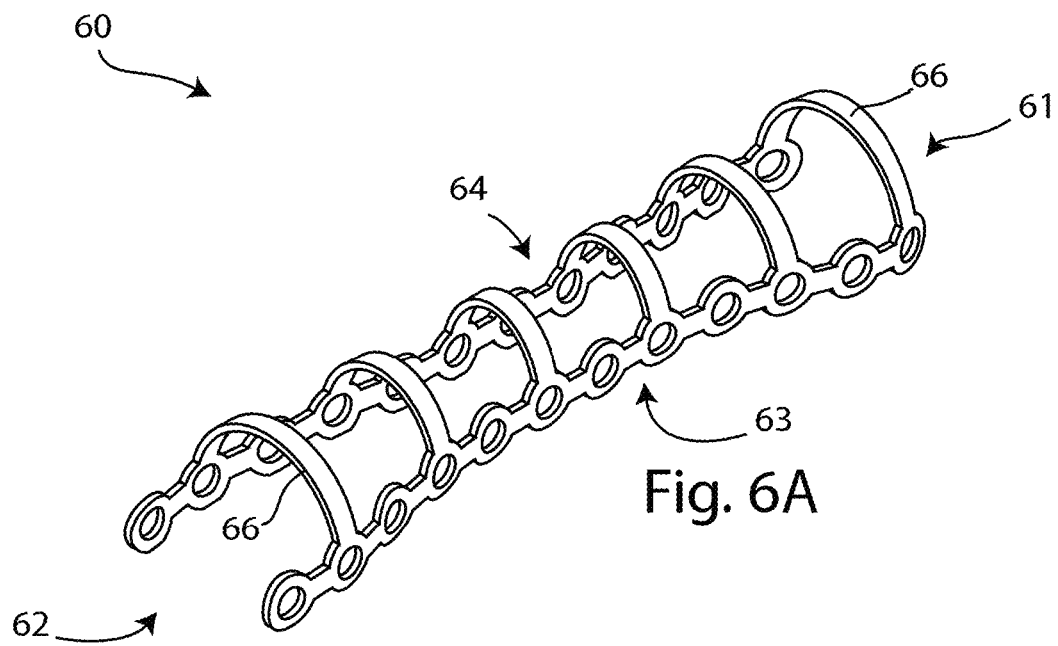
FIG. 6A is an isometric view of an implant in accordance with another example of the present disclosure.
Figure 6B:
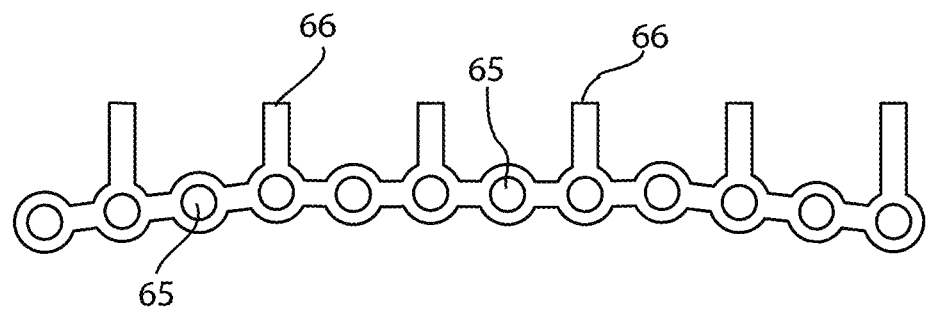
FIG. 6B is a side view of the implant of FIG. 6A.
Figure 6C:
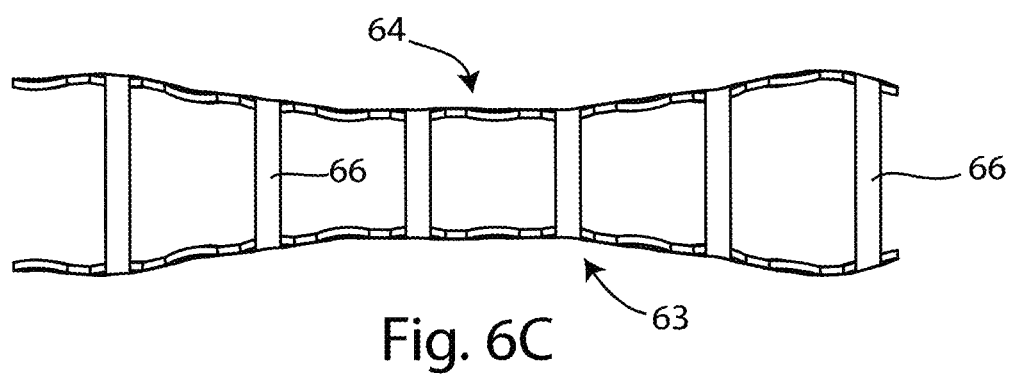
FIG. 6C is a top view of the implant of FIG. 6A.

FIGS. 6A-6C show an implant 60 sized and shaped to reduce fractures in some metacarpal phalanges. The implant 60 has a proximal end 61 and a distal end 62. The implant 60 also has a first portion 63 and a second portion 64 contralateral to each other. The implant 60 may have one or more apertures 65 configured to receive one or more attachment devices (not shown), such as bone screws, to fixedly attached the implant 60 to the bone. The implant 60 may also include at least one third portion 66, intermediate and substantially transverse the first portion 63 and the second portion 64, configured to aid in aligning and holding bone fragments while a surgeon affixes the implant to a bone placed between the first portion 63 and the second portion 64. From a top view the implant 60 may resemble an hour-glass shape. The implant 60 may also resemble a ladder shape.

In one example, the at least one third portion 66 is configured to lie below the flexor or extensor tendons, while the first portion 63 and the second portion 64 engage surfaces of the bone to the sides of the flexor and extensor tendons. In this configuration, the first portion 63 and the second portion 64 act synergistically to provide better stabilization to the bone which allows the thickness of the implant 60 to be much less than it would otherwise need to be. In some examples the thickness of the implant 60 can be about 0.76 mm thick. In other examples, the thickness of the implant 60 can be less than 0.76 mm thick. In yet other examples, the thickness of the implant 60 can be between about 0.76 mm and 2.3 mm thick. Reducing the thickness of the implant 60 reduces the irritation to the patient's soft tissues above the bone including extensor or flexor tendons that may lie above the at least one third portion 66.

Figure 17A:
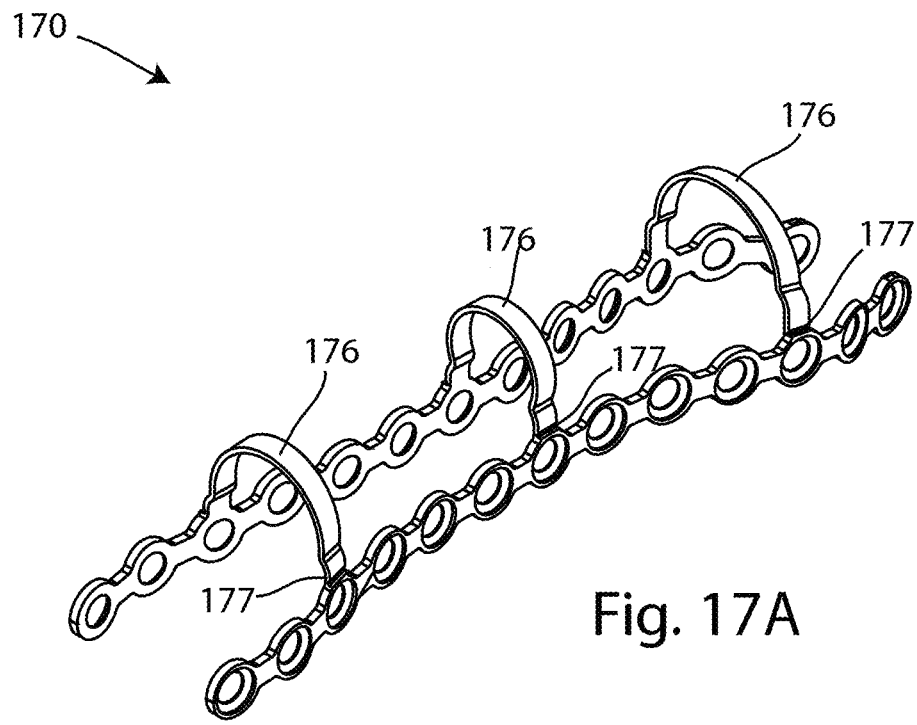
FIG. 17A is an isometric view of an implant in accordance with another example of the present disclosure.
Figure 17B:
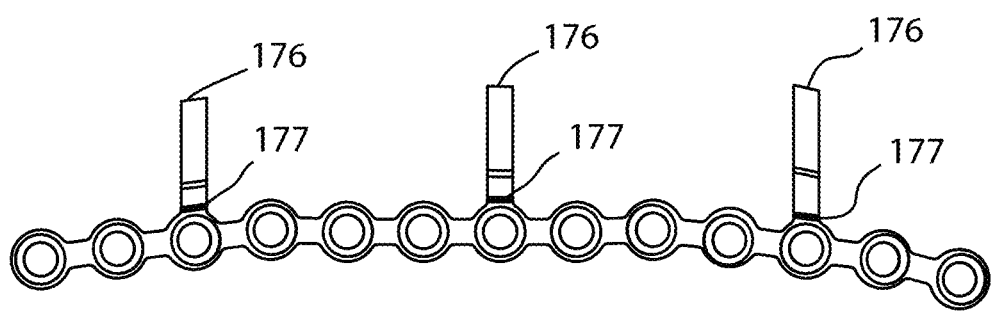
FIG. 17B is a side view of the implant of FIG. 17A.
Figure 17C:
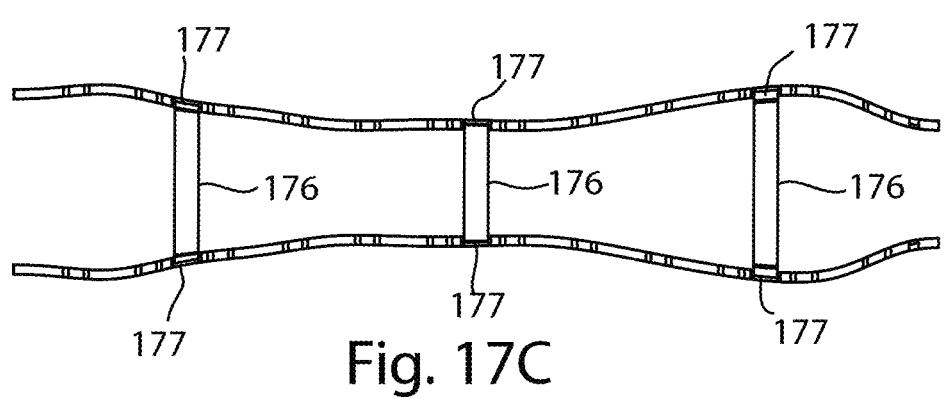
FIG. 17C is a top view of the implant of FIG. 17A.

FIGS. 17A-17C show an alternative implant 170 sized and shaped to reduce fractures in some metacarpal phalanges similar in some respects to that shown in FIGS. 6A-6C. However, the implant 170 shown in FIGS. 17A-17C has at least one third portion 176 which is configured to lie above the flexor or extensor tendon. The implant 170 can also have scored surfaces 177 intermediate the at least one third portion 176 and the first and second portions. This example allows the surgeon to affix the implant 170 to the bone with the at least one third portion over the flexor or extensor tendon. Thus, the surgeon does not have to retract the tendon to one side in order to place the implant around the bone. Once the surgeon affixes the implant 170 to the bone, the surgeon can remove the at least one third portion by bending the at least one third portion relative to the first and second portions to break away the at least one third portion at or near the scored surfaces 177.

FIGS. 7A-7C show an implant 70 sized and shaped to reduce fractures in other metacarpal phalanges. The implant 70 has a proximal end 71 and a distal end 72. The implant 70 also has a first portion 73 and a second portion 74 contralateral to each other. The implant 70 may have one or more apertures 75 configured to receive one or more attachment devices (not shown), such as bone screws, to fixedly attached the implant 70 to the bone. The implant 70 may also include at least one third portion 76, intermediate and substantially transverse the first portion 73 and the second portion 74, configured to aid in aligning and holding bone fragments while a surgeon affixes the implant to a bone placed between the first portion 73 and the second portion 74. The first and second portions 73, 74 may be substantially parallel. The implant 70 may also resemble a ladder shape.

In one example, the at least one third portion 76 is configured to lie below the flexor or extensor tendons, while the first portion 73 and the second portion 74 engage surfaces of the bone to the sides of the flexor and extensor tendons. In this configuration, the first portion 73 and the second portion 74 act synergistically to provide better stabilization to the bone which allows the thickness of the implant 70 to be much less than it would otherwise need to be. In some examples the thickness of the implant 70 can be about 0.76 mm thick. In other examples, the thickness of the implant 70 can be less than 0.76 mm thick. In yet other examples, the thickness of the implant 70 can be between about 0.76 mm and 2.3 mm thick. Reducing the thickness of the implant 70 reduces the irritation to the patient's soft tissues above the bone including extensor or flexor tendons that may lie above the at least one third portion 76.

Figure 18A:
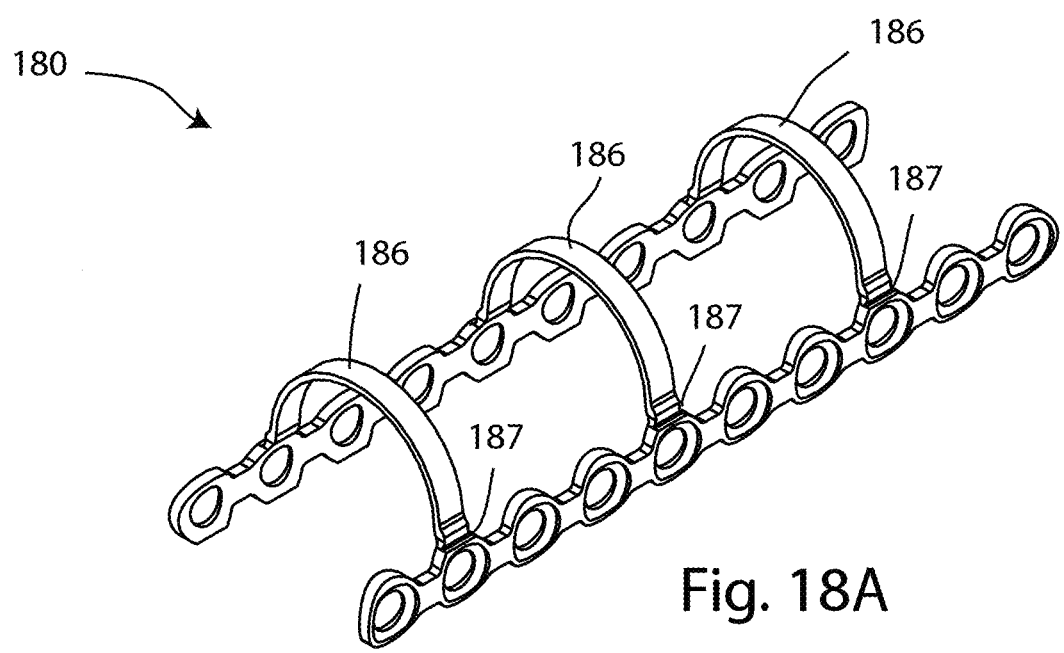
FIG. 18A is an isometric view of an implant in accordance with another example of the present disclosure.
Figure 18B:
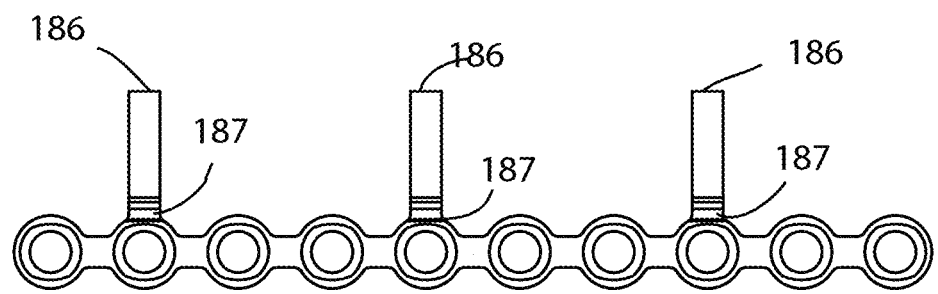
FIG. 18B is a side view of the implant of FIG. 18A.
Figure 18C:
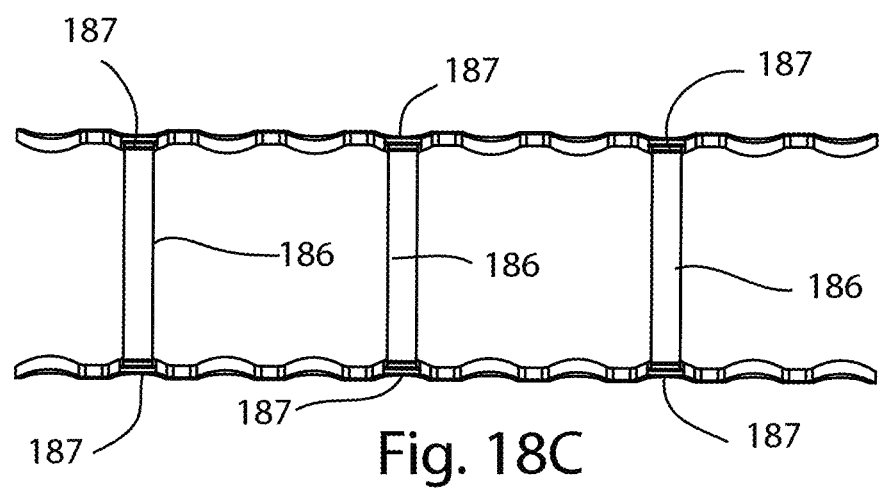
FIG. 18C is a top view of the implant of FIG. 18A.
Figure 21A:
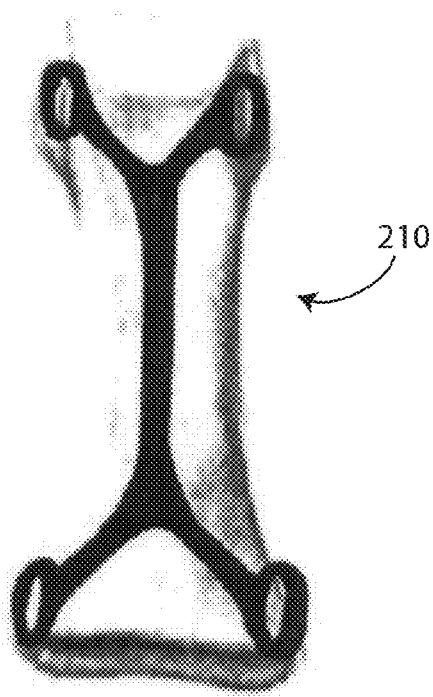
FIG. 21A is a top view of an implant attached to a tubular bone in accordance with another example of the present disclosure.
Figure 21B:
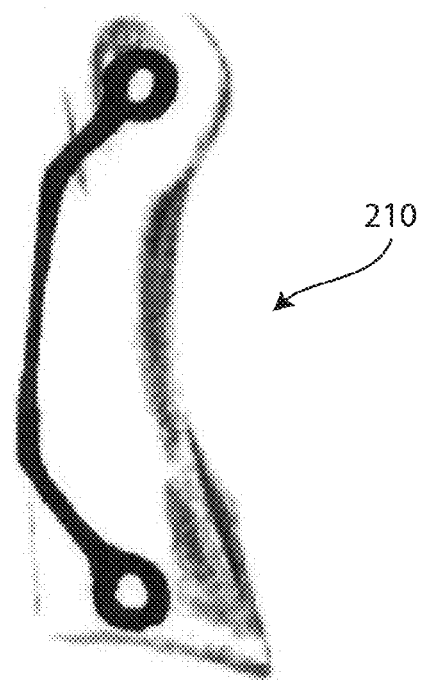
FIG. 21B is a side view of the implant of FIG. 21A.
Figure 22A:
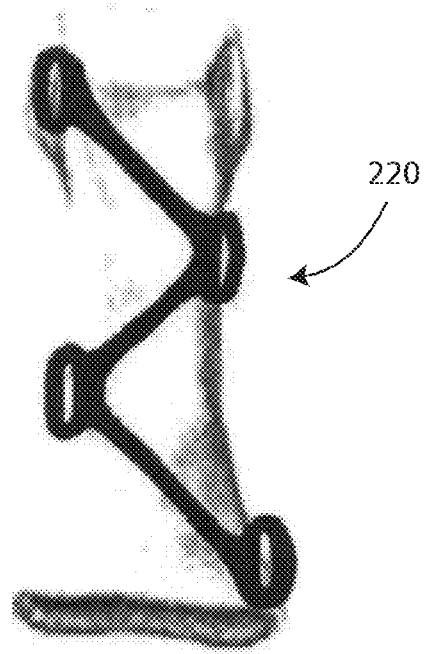
FIG. 22A is a top view of an implant attached to a tubular bone in accordance with another example of the present disclosure.
Figure 22B:
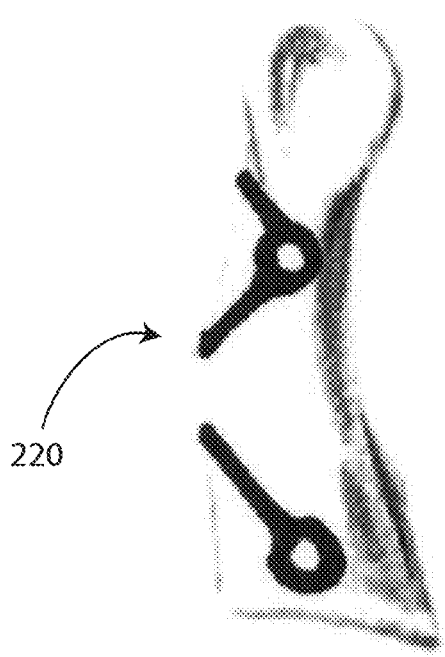
FIG. 22B is a side view of the implant of FIG. 22A.
Figures 23A, 23B:
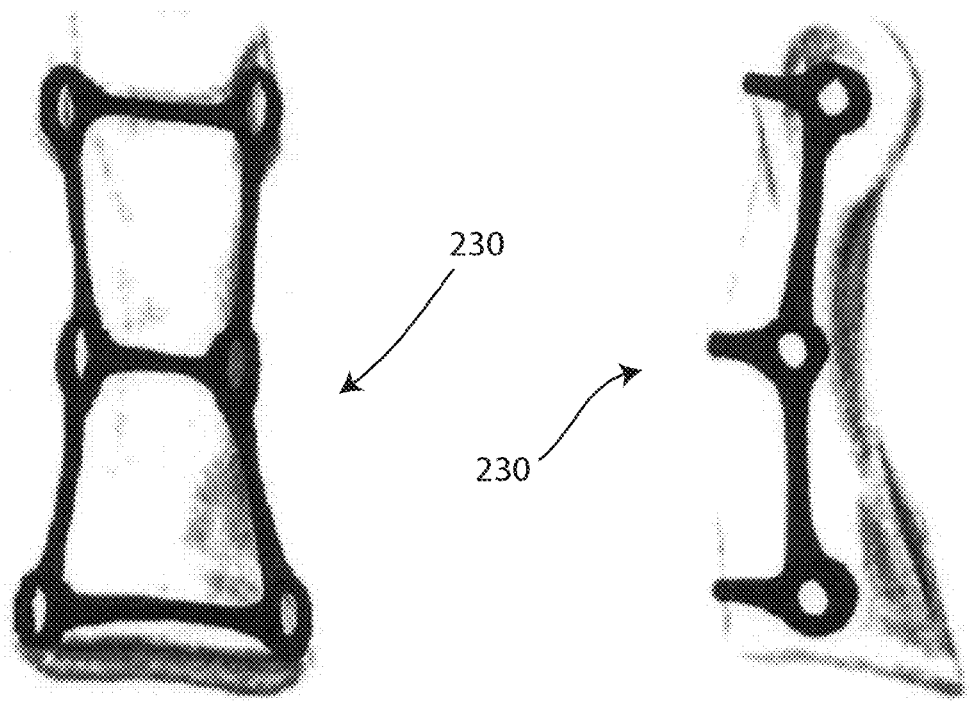
FIG. 23A is a top view of an implant attached to a tubular bone in accordance with another example of the present disclosure.
FIG. 23B is a side view of the implant with FIG. 23A.

FIGS. 18A-18C show an alternative implant 180 sized and shaped to reduce fractures in other metacarpal phalanges similar in some respects to that shown in FIGS. 7A-7C. However, the implant 180 shown in FIGS. 18A-18C has at least one third portion 186 which is configured to lie above the flexor or extensor tendon. The implant 180 can also have scored surfaces 187 intermediate the at least one third portion 186 and the first and second portions. This example allows the surgeon to affix the implant 180 to the bone with the at least one third portion over the flexor or extensor tendon. Thus, the surgeon does not have to retract the tendon to one side in order to place the implant around the bone. Once the surgeon affixes the implant 180 to the bone, the surgeon can remove the at least one third portion by bending the at least one third portion relative to the first and second portions to break away the at least one third portion at or near the scored surfaces 187.

FIG. 8 shows how the different size and shape implants 81, 82, 83, and 84 can be utilized to anatomically reduce fractures in different size and shape bones of a human hand 80.

In other examples, the at least one third portion can be separable from the first portion and the second portion without cutting the at least one third portion. FIGS. 9A-9F illustrate one such implant 90. In this example, the at least one third portion 96 can have one or more attachment members 97 configured to interact with one or more surfaces of the first and second portions 93, 94 to rigidly hold the first and second portions 93, 94 in alignment and provide alignment forces while the surgeon affixes the implant to the bone fragments. In a particular example, the at least one third portion 96 can be made of a semi-rigid plastic and the attachment members 97 can be plastic tabs which interact with one or more of the apertures 95 formed in the first and second portions 93, 94. In other examples, the attachment members 97 can be slots formed in the at least one third portion 96 configured to receive one or more surfaces of the first and second portions 93, 94.

The at least one third portion 96 can also be provided with one or more release members 98 to help facilitate removal of the at least one third portion 96 once the first and second portions 93, 94 have been attached to the bone. In practice, the surgeon can squeeze the release members 98 toward each other causing the at least one third portion 96 to spread apart with sufficient force to disengage the attachment members 97 from the first and second portions 93, 94. The surgeon can also push the release members 98 away from each other to increase the alignment forces imparted to the first and second portions 93, 94 by the at least one third portion 96 during placement of the implant.

Figure 11A:
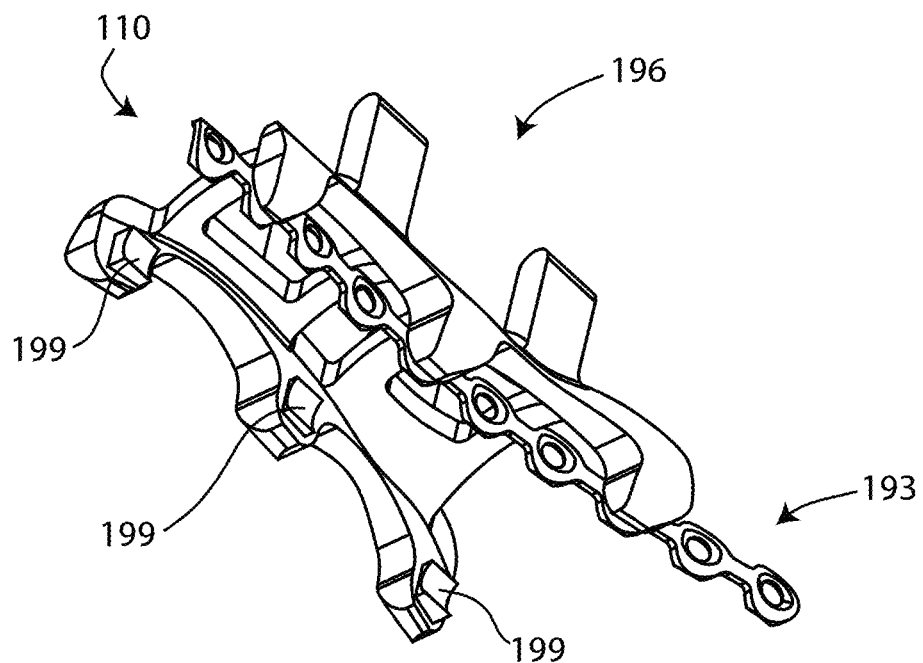
FIG. 11A is a top isometric view of an implant system in accordance with another example of the present disclosure.
Figure 11B:
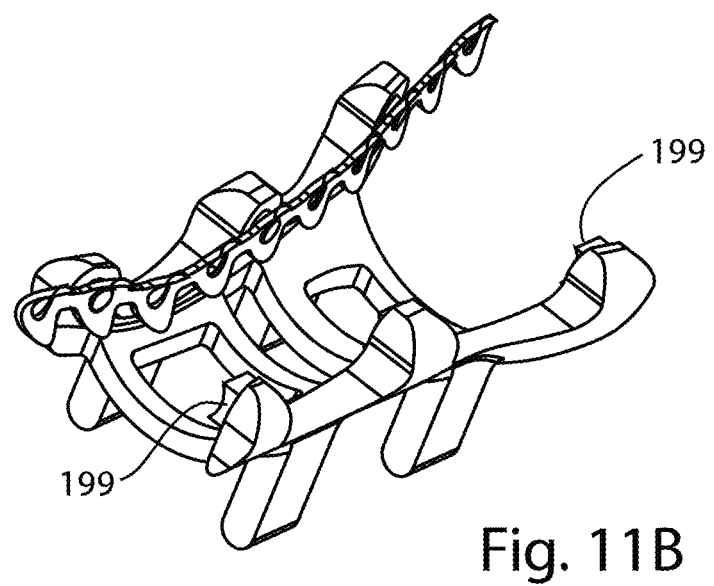
FIG. 11B is a bottom isometric view of the implant system of FIG. 11A.
Figure 11C:
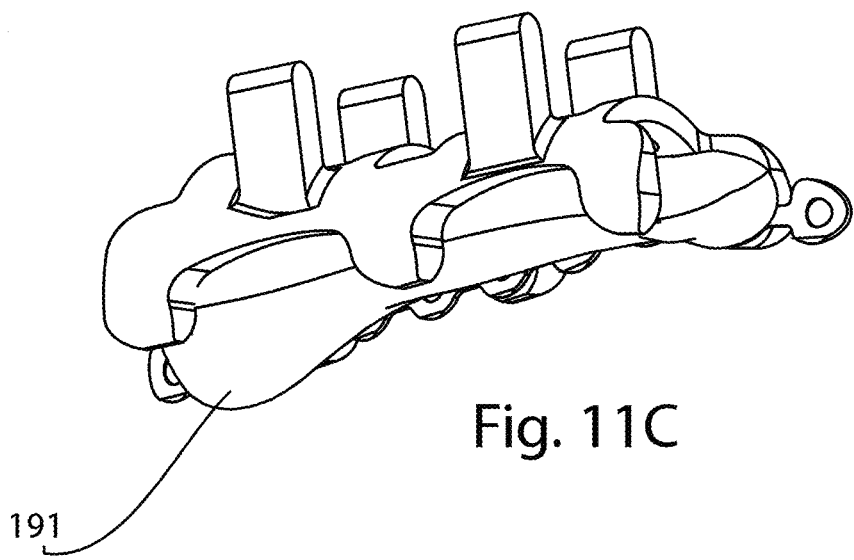
FIG. 11C is a left-side isometric view of the implant system of FIG. 11A attached to a bone.
Figure 11D:
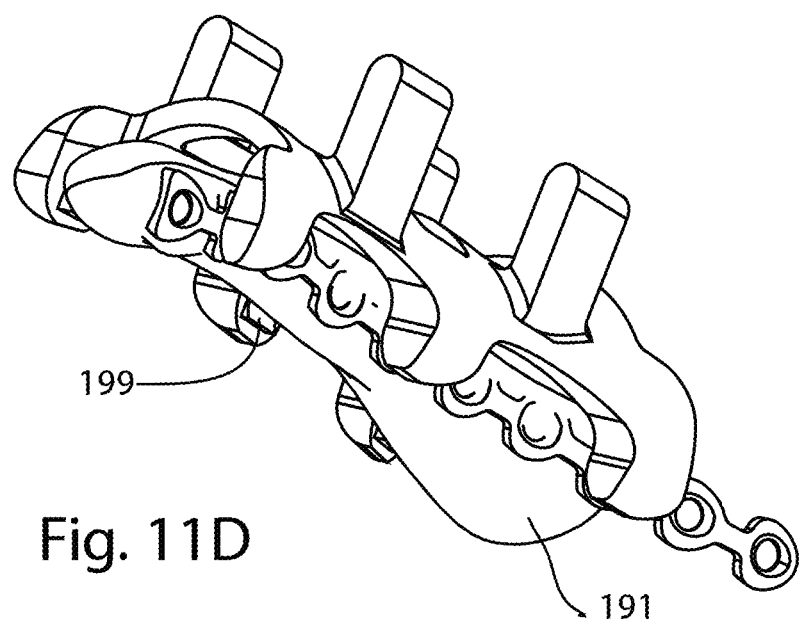
FIG. 11D is a right-side isometric view of the implant system of FIG. 11A attached to a bone.

FIGS. 11A-11D illustrate another example implant 110 similar to that shown in FIGS. 9A-9F, except this embodiment has only a first portion 193 and at least one third portion 196. The at least one third portion 196 can have one or more engaging surfaces 199 that can clasp and align the bone 191 while the surgeon attaches the first portion 193 to the bone, as can be seen in FIGS. 11C and 11D. The one or more engaging surfaces 199 can directly engage the bone 191 or indirectly engage the bone through soft tissues, etc. Once the first portion 193 is affixed to the bone, the at least one third portion 196 can be removed in a similar fashion as described above with reference to FIGS. 9A-9F.

In yet other examples, one or more removable ratcheting clamps (not shown) can be attached to the first and second portions and anatomically shaped by a towel clamp (not shown) to provide reduction forces between the first and second portions. Once the first and second portions are fixed to the bone, the ratcheting clamps can be removed. In a particular example, a bending instrument (not shown) can be used to simultaneously bend the implant and act as a drill guide.

Figure 10A:
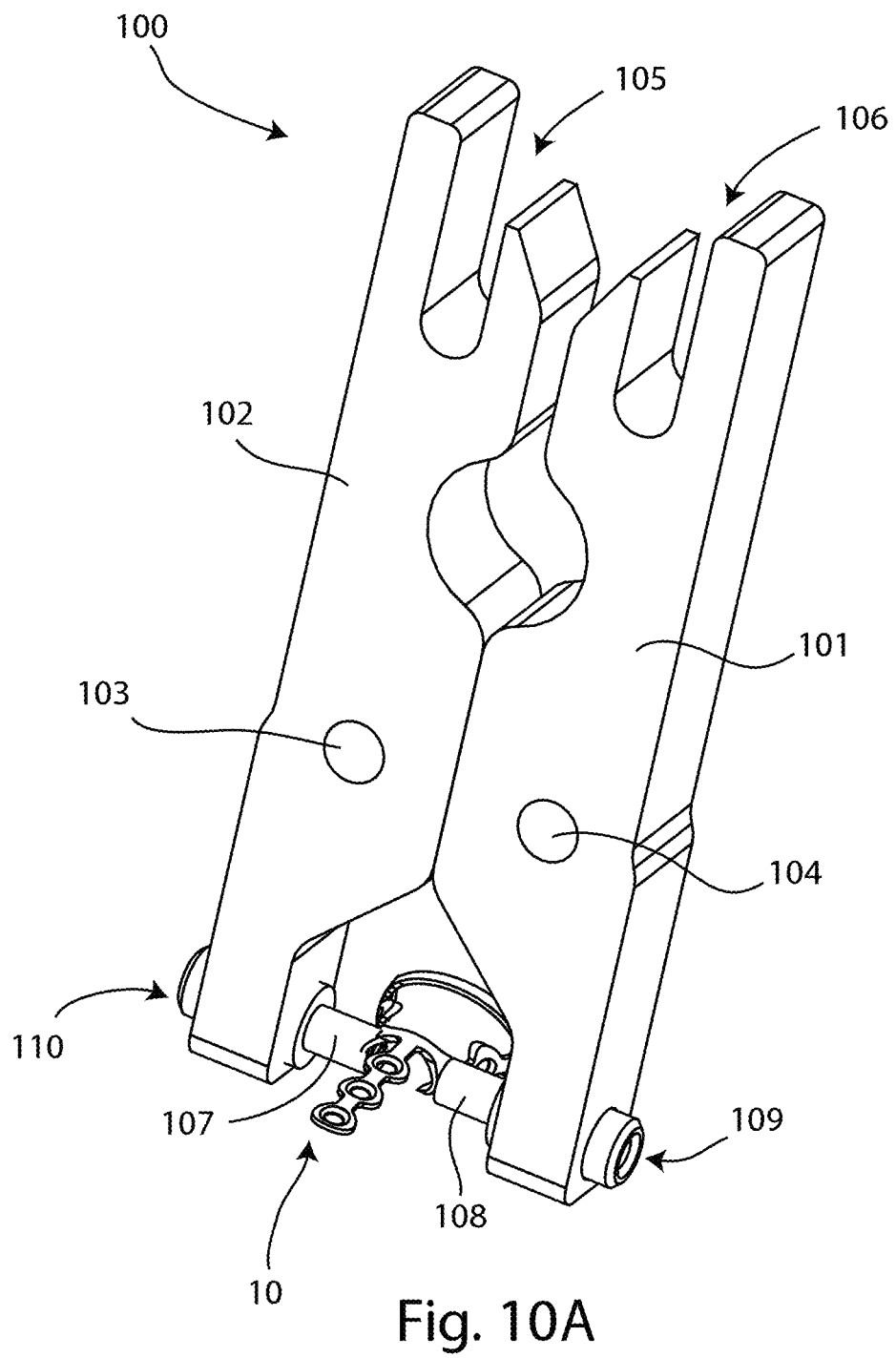
FIG. 10A is an isometric view of a drill guide instrument in accordance with one example of the present disclosure.
Figure 10B:
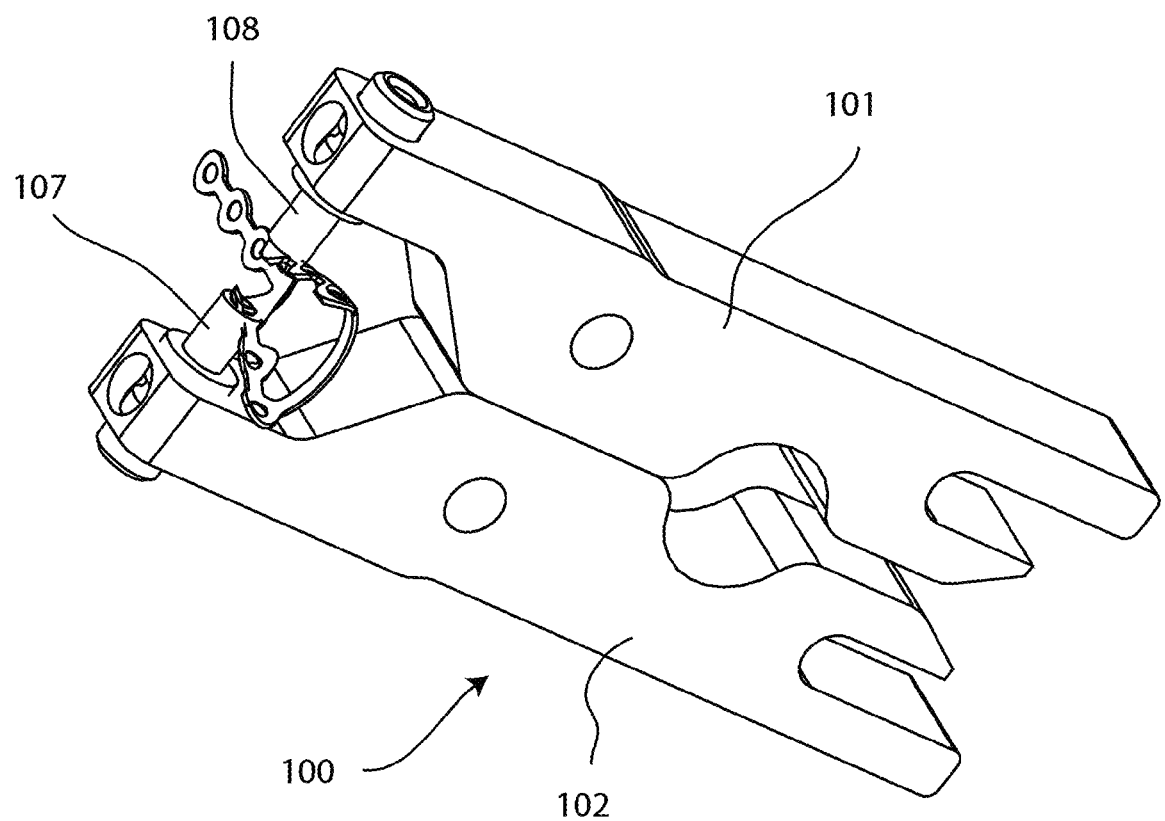
FIG. 10B is another isometric view of the drill guide instrument of FIG. 10A.

FIGS. 10A-10B show an implant 10 engaged to a drill guide assembly 100. The drill guide assembly 100 can have drill guides 109, 110 inserted into assembly alignment members 101 and 102. The drill guides 109, 110 can have hollow drill guide shafts 107, 108. The assembly alignment members 101, 102 can interact with a suitable tool, such as parallel pliers (not shown), through apertures 103, 104 and slots 105, 106 to ensure that the drill guides 109, 110 remain in alignment with each other as the drill guides 109, 110 are brought closer to each other to engage contralateral apertures formed in the implant 10. The tips of the drill guides 109, 110 (not shown) may have surfaces or structures which interact with complimentary shaped surfaces formed in the implant. For example, the tips of the drill guides 109, 110 may have nipples or lips which fit into complimentary shaped surfaces formed in the apertures of the implant to help align the drill guides 109, 110 with the implant.

Figures 24A, 24B:
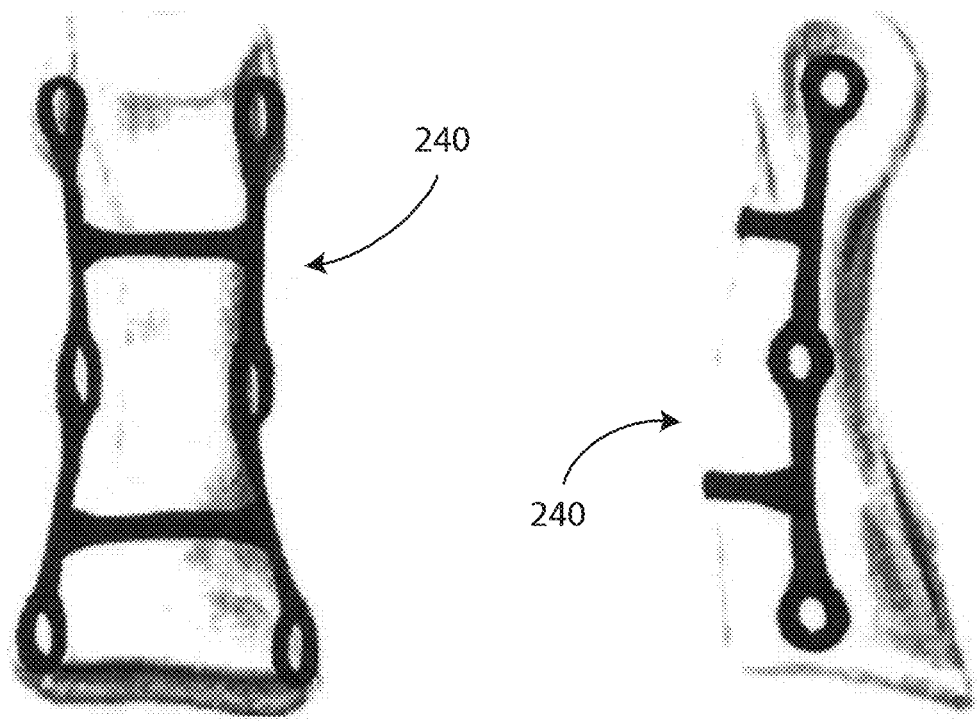
FIG. 24A is a top view of an implant attached to a tubular bone in accordance with another example of the present disclosure.
FIG. 24B is a side view of the implant of FIG. 24A.

FIGS. 19A-24B show various examples of implants according to other examples of the present disclosure. FIGS. 19A-19B show a top view and a side view of a box style implant 190 attached to a bone. FIGS. 20A-20B show a top view and a side view of a diamond shaped implant 200 attached to a bone. FIGS. 21A-21B a top view and a side view of an hourglass or I-beam shaped implant 210 attached to a bone. FIGS. 22A-22B show a top view and a side view of a zigzag or offset shaped implant 22A attached to a bone. FIGS. 23A-23B show a top view and a side view of a ladder shaped implant attached to a bone with aperture holes located at the junctions of the latter pieces. FIG. 24A-24B show a top view and a side view of a modified ladder shaped implant attached to a bone with aperture holes located intermediate the junctions of the ladder pieces.

It will be appreciated by one skilled in the art that various instruments can be used to surgically implant the preceding devices described above. Some example instruments may include: bone biopsy needles, a drill, an awl, a reamer, dilators and/or ports, guide wires, graspers, cutters, drill guides, parallel pliers, etc. Some or all of the implants and instruments disclosed herein may be included in one or more kits to enable the surgeon maximum flexibility to fix any fracture the surgeon encounters during surgery.

Methods of inserting the implants disclosed herein may include: forming an incision to access the fractured bone, retracting the tendon to either side of the bone to provide access to the surface of the bone, placing the implant on the bone and securing it to the bone, releasing the tendon and closing the incision.

Other methods of inserting the implants disclosed herein may include: forming an incision to access the fractured bone, placing the at least one third portion of the implant over the tendon on the bone and securing it to the bone, removing the at least one third portion of the implant by cutting or applying a force, and then closing the incision.

It should be understood that the present components, systems, kits, implants, and methods are not intended to be limited to the particular forms disclosed. Rather, they are intended to include all modifications, equivalents, and alternatives falling within the scope of the claims. They are further intended to include examples which may be formed by combining features from the disclosed examples, and variants thereof.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

The present invention may be embodied in other specific forms without departing from its spirit or essential characteristics. It is appreciated that various features of the above-described examples can be mixed and matched to form a variety of other alternatives. For example, a plate configuration or stabilization component from one example may be combined with a plate configuration from another example. Similarly, manufacturing or assembly methods described for one implant may be used in the manufacture or assembly of another implant. As such, the described examples are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An implant for repairing a fracture in a bone, the bone including a first surface and a second surface spaced apart from and contralateral to the first surface, a flexor tendon coupled to and extending along a longitudinal axis of the bone on one side of the bone, and an extensor tendon coupled to and extending along the longitudinal axis of the bone on the side contralateral to the flexor tendon, the implant comprising:

a first portion configured to engage the first surface of the bone, the first portion having a first length and a first plurality of apertures, the first portion also having two terminal ends spaced apart from one another by the first length, each of the first plurality of apertures extending entirely through the first portion, the first portion including two opposed major surfaces presented in opposite directions throughout the first length, the first portion also including (a) two end segments spaced apart from one another along the first length and (b) an intermediate segment disposed between the end segments along the first length, each end segment of the first portion including a different one of the terminal ends of the first portion and a section of said end segment adjacent to said different one of the terminal ends;

a second portion configured to engage the second surface of the bone, the second portion being contralateral to the first portion, the second portion having a second length and a second plurality of apertures, the second portion also having two terminal ends spaced apart from one another by the second length, each of the second plurality of apertures extending entirely through the second portion, the second length being substantially equal to the first length, the second portion including two opposed major surfaces presented in opposite directions throughout the second length, the second portion also including (c) two end segments spaced apart from one another along the second length and (d) an intermediate segment disposed between the end segments along the second length, each end segment of the second portion including a different one of the terminal ends of the second portion and a section of said end segment adjacent to said different one of the terminal ends of the second portion, the intermediate segment of the second portion being disposed opposite and spaced apart from the intermediate segment of the first portion, each of the end segments of the second portion being disposed opposite and spaced apart from a corresponding end segment of the first portion, the intermediate segment of the second portion being spaced apart from the intermediate segment of the first portion by a smaller distance than the end segments of the second portion are spaced apart from the corresponding end segments of the first portion such that the implant resembles an hourglass, at least one of the terminal ends of the second portion being spaced apart from the corresponding terminal end of the first portion by a distance that is smaller than a distance by which the section of the end segment of the second portion adjacent to said at least one of the terminal ends of the second portion is spaced apart from the section of the corresponding end segment of the first portion adjacent to said corresponding terminal end of the first portion, one of the opposed major surfaces of the second portion being presented toward one of the opposed major surfaces of the first portion throughout the first and second lengths; and at least two third portions configured to extend from proximate the first surface of the bone to proximate the second surface of the bone, each of the at least two third portions being free of any aperture and engaging the first portion and the second portion to apply an alignment biasing force to the bone, each of the at least two third portions extending (e) in an arch transverse to the first length of the first portion and transverse to the second length of the second portion and (f) from adjacent an aperture of the first plurality of apertures to adjacent an aperture of the second plurality of apertures, each of the at least two third portions being spaced apart from and substantially parallel to every other of the at least two third portions along the first length and along the second length such that the implant resembles a ladder, each of the at least two third portions being spaced apart from every other of the at least two third portions along the first length by at least one of the first plurality of apertures and along the second length by at least one of the second plurality of apertures.

2. The implant of claim 1, wherein each of the at least two third portions is configured to lie above at least one of the flexor tendon and the extensor tendon.

3. The implant of claim 1, wherein the at least another portion further comprises at least one attachment member configured to be engaged by the at least one attachment member.

4. The implant of claim 1, wherein the at least two third portions are made of a semi-rigid plastic.

5. The implant of claim 1, wherein at least one of the first portion and the at least two third portions comprises at least one of titanium and stainless steel.

6. The implant of claim 5, wherein the first portion is between about 0.38 mm and 1.2 mm thick.

7. The implant of claim 5, wherein the first portion is between about 0.46 mm and 1.7 mm thick.

8. The implant of claim 5, wherein the first portion is between about 0.76 mm and 2.3 mm thick.

9. The implant of claim 1, further comprising at least two scored surfaces, each of the at least two scored surfaces being disposed between (a) a corresponding third portion of the at least two third portions and (b) at least one of the first portion and the second portion.

10. The implant of claim 9, wherein each of the at least two third portions is configured to be disengaged from at least one of the first portion and the second portion by bending each of the at least two third portions relative to at least one of the first portion and the second portion proximate the at least two scored surfaces until the at least two third portions break away from at least one of the first surface and the second surface.

11. The implant of claim 1, wherein each of the at least two third portions is configured to disengage at least one of the first portion and the second portion after the one of the first portion and the second portion engages the first surface and the second surface, respectively.

12. The implant of claim 3, wherein the at least one attachment member is configured to disengage the at least one attachment surface after the first portion is affixed to the bone.

13. The implant of claim 12, further comprising at least one release member configured to apply a force in a direction to the at least one attachment member to disengage the at least one attachment member from the at least one attachment surface.

14. The implant of claim 13, wherein the at least one release member is configured to apply another force in another direction to increase the alignment biasing force applied by the at least another portion to the bone.

15. The implant of claim 9, wherein each of the at least two scored surfaces extends in a direction substantially parallel to at least one of the first length and the second length, each of the at least two scored surfaces including a score extending across the scored surface from one edge to an opposite edge in the direction substantially parallel to at least one of the first length and the second length.

16. An implant for repairing a fracture in a bone, the bone including a first surface and a second surface spaced apart from and contralateral to the first surface, a flexor tendon coupled to and extending along a longitudinal axis of the bone on one side of the bone, and an extensor tendon coupled to and extending along the longitudinal axis of the bone on the side contralateral to the flexor tendon, the implant comprising:

a first portion configured to engage the first surface of the bone, the first portion having a first length and a first plurality of apertures, the first portion also having two terminal ends spaced apart from one another by the first length, each of the first plurality of apertures extending entirely through the first portion, the first portion including two opposed major surfaces presented in opposite directions throughout the first length, the first portion also including (a) two end segments spaced apart from one another along the first length and (b) an intermediate segment disposed between the end segments along the first length, each end segment of the first portion including a different one of the terminal ends of the first portion and a section of said end segment adjacent to said different one of the terminal ends;

a second portion configured to engage the second surface of the bone, the second portion being contralateral to the first portion, the second portion having a second length and a second plurality of apertures, the second portion also having two terminal ends spaced apart from one another by the second length, each of the second plurality of apertures extending entirely through the second portion, the second portion including two opposed major surfaces presented in opposite directions throughout the second length, the second portion also including (c) two end segments spaced apart from one another along the second length and (d) an intermediate segment disposed between the end segments along the second length, each end segment of the second portion including a different one of the terminal ends of the second portion and a section of said end segment adjacent to said different one of the terminal ends of the second portion, the intermediate segment of the second portion being disposed opposite and spaced apart from the intermediate segment of the first portion, each of the end segments of the second portion being disposed opposite and spaced apart from a corresponding end segment of the first portion, the intermediate segment of the second portion being spaced apart from the intermediate segment of the first portion by a smaller distance than the end segments of the second portion are spaced apart from the corresponding end segments of the first portion such that the implant resembles an hourglass, at least one of the terminal ends of the second portion being spaced apart from the corresponding terminal end of the first portion by a distance that is smaller than a distance by which the section of the end segment of the second portion adjacent to said at least one of the terminal ends of the second portion is spaced apart from the section of the corresponding end segment of the first portion adjacent to said corresponding terminal end of the first portion, one of the opposed major surfaces of the second portion being presented toward one of the opposed major surfaces of the first portion throughout the first and second lengths;

at least two third portions configured to extend from proximate the first surface of the bone to proximate the second surface of the bone, each of the at least two third portions being free of any aperture and engaging the first portion and the second portion to impart an alignment biasing force to the bone, each of the at least two third portions extending (e) in an arch transverse to the first length of the first portion and transverse to the second length of the second portion and (f) from adjacent an aperture of the first plurality of apertures to adjacent an aperture of the second plurality of apertures, each of the at least two third portions being spaced apart from and substantially parallel to every other of the at least two third portions along the first length and along the second length such that the implant resembles a ladder, each of the at least two third portions being spaced apart from every other of the at least two third portions along the first length by at least one of the first plurality of apertures and along the second length by at least one of the second plurality of apertures; and at least two scored surfaces, each of the at least two scored surfaces being disposed between a corresponding third portion of the at least two third portions and at least one of the first portion and the second portion, each of the at least two scored surfaces extending in a direction substantially parallel to at least one of the first length and the second length, each of the at least two scored surfaces including a score extending across the scored surface from one edge to an opposite edge in the direction substantially parallel to at least one of the first length and the second length, each of the at least two scored surfaces enabling the corresponding third portion of the at least two third portions to disengage the at least one of the first portion and the second portion after the one of the first portion and the second portion engages one of the first surface and the second surface, respectively.

17. The implant of claim 16, wherein each of the at least two third portions is configured to lie below at least one of the flexor tendon and the extensor tendon.

18. The implant of claim 16, wherein each of the at least two third portions is configured to lie above at least one of the flexor tendon and the extensor tendon.

19. The implant of claim 16, wherein the at least one third portion further comprises at least one attachment member and wherein at least one of the first portion and the second portion comprises at least one attachment surfaces configured to be engaged by the at least one attachment member.

20. The implant of claim 16, wherein the at least two third portions are made of a semi-rigid plastic.

21. The implant of claim 16, wherein at least one of the first portion, the second portion, and the at least two third portions comprises at least one of titanium and stainless steel.

22. The implant of claim 21, wherein at least one of the first portion, the second portion, and the at least two third portions is between about 0.38 mm and about 1.2 mm thick.

23. The implant of claim 21, wherein at least one of the first portion, the second portion, and the at least two third portions is between about 0.46 mm and about 1.7 mm thick.

24. The implant of claim 21, wherein at least one of the first portion, the second portion, and the at least two third portions is between about 0.76 mm and about 2.3 mm thick.

25. The implant of claim 19, wherein the at least one attachment member is configured to disengage the at least one attachment surface after at least one of the first portion and the second portion are affixed to the bone.

26. The implant of claim 25, further comprising at least one release member configured to apply a force in a direction to disengage the at least one attachment member from the at least one attachment surface.

27. The implant of claim 26, wherein the at least one release member is configured to apply another force in another direction to increase the alignment biasing force applied by the at least one third portion to the bone.

* * * * *